US012592769B2

(12) United States Patent
Jain et al.

(10) Patent No.: US 12,592,769 B2
(45) Date of Patent: \*Mar. 31, 2026

(54) BODY AREA NETWORK WITH BISTATIC WIRELESS BACKSCATTERING DEVICES

(71) Applicant: Robert Bosch GmbH, Stuttgart (DE)

(72) Inventors: Vivek Jain, Sunnyvale, CA (US);
Kaustubh Gandhi, Filderstadt (DE);
Sushanta Mohan Rakshit, Milpitas,
CA (US); Abhinav Kunchamwar,
Stuttgart (DE)

(73) Assignee: Robert Bosch GmbH, Stuttgart (DE)

( * ) Notice: Subject to any disclaimer, the term of this
patent is extended or adjusted under 35
U.S.C. 154(b) by 124 days.

This patent is subject to a terminal dis-
claimer.

(21) Appl. No.: 18/341,256

(22) Filed: Jun. 26, 2023

(65) Prior Publication Data

US 2024/0430000 A1 Dec. 26, 2024

(51) Int. Cl.
*H04B 7/22* (2006.01)
*A61B 5/00* (2006.01)
*H04B 7/26* (2006.01)

(52) U.S. Cl.
CPC ............. *H04B 7/22* (2013.01); *A61B 5/0024*
(2013.01); *H04B 7/2643* (2013.01)

(58) Field of Classification Search
CPC ........ H04B 7/22; H04B 7/2643; H04B 7/265;
H04B 7/2656; H04B 7/2659; H04B
7/2646; A61B 5/0024
See application file for complete search history.

(56) References Cited

U.S. PATENT DOCUMENTS

| | | | |
|---|---|---|---|
| 8,913,628 B2 | 12/2014 | Patel et al. | |
| 11,457,490 B2 | 9/2022 | Katan Baf Nezhad et al. | |
| 11,503,545 B2 | 11/2022 | Katan Baf Nezhad et al. | |
| 2018/0167266 A1 | 6/2018 | Subramani et al. | |
| 2019/0313352 A1 | 10/2019 | Do et al. | |
| 2019/0380583 A1 | 12/2019 | Danneels et al. | |
| 2020/0169318 A1* | 5/2020 | Kim ..................... | H04B 17/309 |
| 2021/0204213 A1* | 7/2021 | Lee ..................... | G06K 19/0723 |
| 2022/0386348 A1* | 12/2022 | Zhang ................... | H04W 72/23 |
| 2023/0284123 A1* | 9/2023 | Ge ......................... | H04L 5/0048 |
| | | | 370/329 |
| 2024/0163840 A1* | 5/2024 | Säily ....................... | G01S 7/006 |

OTHER PUBLICATIONS

Atmosic Technologies, "The Wolds Most Energy Efficient IoT
Solutions: Product Portfolio", 2023, 6 pages.

(Continued)

*Primary Examiner* — Khanh C Tran

(74) *Attorney, Agent, or Firm* — BROOKS KUSHMAN
P.C.

(57) ABSTRACT

Configuring and utilizing a body area network (BAN) is
provided. In a configuration phase, configuration messages
are sent for scheduling a plurality of backscatter devices
such that during a data collection phase each of the plurality
of backscatter devices is configured to transmit in an indi-
vidually-assigned time slot. In the data collection phase, a
data collector device receives, from the plurality of backs-
catter devices, sensor data messages including sensor data
from the backscatter devices, the sensor data messages being
scheduled according to the configuration phase.

29 Claims, 14 Drawing Sheets

100

Head Band
Sensor
102A

In-Ear Sensor
102B

In-Ear Sensor
102C

Spine Sensor
102D

Chest Sensor
102E

Wrist Sensor
102F

Wrist Sensor
102G

Wrist Sensor
102H

Wrist Sensor
102I

Shoe Sensor
102J

(56) References Cited

OTHER PUBLICATIONS

Amjad et al., "Energy Efficient Resource Allocation for eHealth Monitoring Wireless Body Area Networks with Backscatter Communication", IEEE Sensors Journal, Aug. 2022, pp. 16638-16651, vol. 22, No. 16.

Katanbaf et al., "Relacks: Reliable Backscatter Communication in Indoor Environments", Proc. ACM Interact. Mob. Wearable Ubiquitous Technology, Jun. 2020, pp. 1-24, vol. 4, No. 2, Article 48.

Khaleghi et al., "Radio Frequency Backscatter Communication for High Data Rate Deep Implants", IEEE Trans. On Microwave Theory and Techniques, Jul. 2018, 14 pages, vol. 67, No. 3.

Khan et al., "Wireless Power Transfer Techniques for Implantable Medical Devices: A Review", Sensors, Jun. 19, 2020, pp. 1-58, vol. 20, No. 3487.

Song et al., Advances in Wirelessly Powered Backscatter Communications: From Antenna/RF Circuitry Design to Printed Flexible Electronics, Proceedings of the IEEE, Jun. 18, 2021, pp. 1-22.

Inplay Inc., "InPlay's NanoBeacon Named RFID Journal's Best New Product of 2021" AP News, Sep. 30, 2021, 3 pages.

Ukkonen et al., "Backscattering-Based Wireless Communication and Power Transfer to Small Biomedical Implants", Proc. of SPIE, Feb. 21, 2020, 7 pages, vol. 11235.

Seymour, "Wake Bluetooth from Deep Sleep Using an RF Signal", Silicon Labs Live: Wireless Connectivity Tech Talks, Aug. 20, 2020, 32 pages.

Bosch, "BHI260AP Datasheet", Apr. 15, 2021, pp. 1-173.

Wikipedia, "Body Area Network", Jun. 22, 2023, 6 pages.

Wikipedia, "Carrier-Sense Multiple Access", Jul. 21, 2023, 3 pages.

Wikipedia, "Energy Harvesting", Jul. 31, 2023, 17 pages.

Wikipedia, "IEEE 802.15.6", Jun. 22, 2023, 2 pages.

Wikipedia, "Manchester Code", Jul. 31, 2023, 4 pages.

Wikipedia, "On-Off Keying", Jul. 31, 2023, 1 page.

Wikipedia, "Radio-Frequency Identification", Jul. 31, 2023, 31 pages.

Zang et al., "Throughput Improvement in Backscatter-Based Wireless Body Area Network", IEEE International Conference on Human-Machine Systems (ICHMS), Sep. 2020, 6 pages.

Zhang et al., "FreeRider: Backscatter Communication Using Commodity Radios", CoNEXT '17: Proceedings of the 13th International Conference on Emerging Networking Experiments and Technologies, Nov. 2017, pp. 389-401.

Priyankara et al., "A Clustering Method for Wireless Sensor Networks with Heterogeneous Node Types", IEICE Trans. Commun., Aug. 2011, vol. E94-B, No. 8, pp. 2254-2264.

Shiraishi et al., "Query Timing Analysis for Content-Based Wake-Up Realizing Informative IoT Data Collection", IEEE Wireless Communications Letters, Feb. 2023, vol. 12, No. 2, pp. 327-331.

Ullah et al., "MAC Hurdles in Body Sensor Networks", Advanced Communication Technology, Feb. 2009, pp. 1151-1155.

* cited by examiner

*100*

*200A*

*200B*

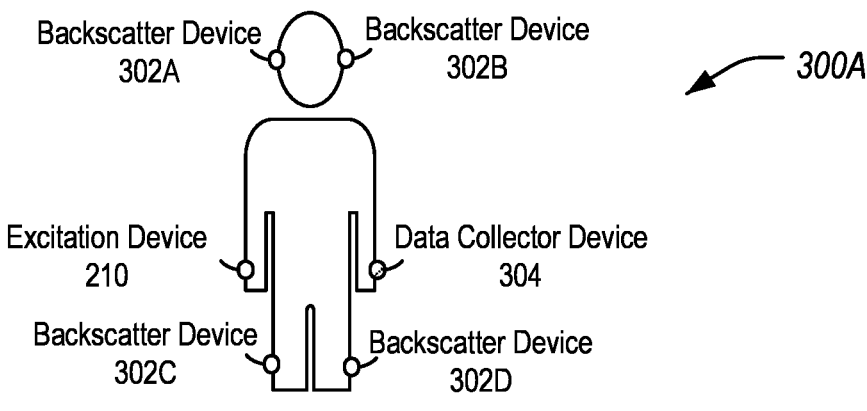
FIG. 3A
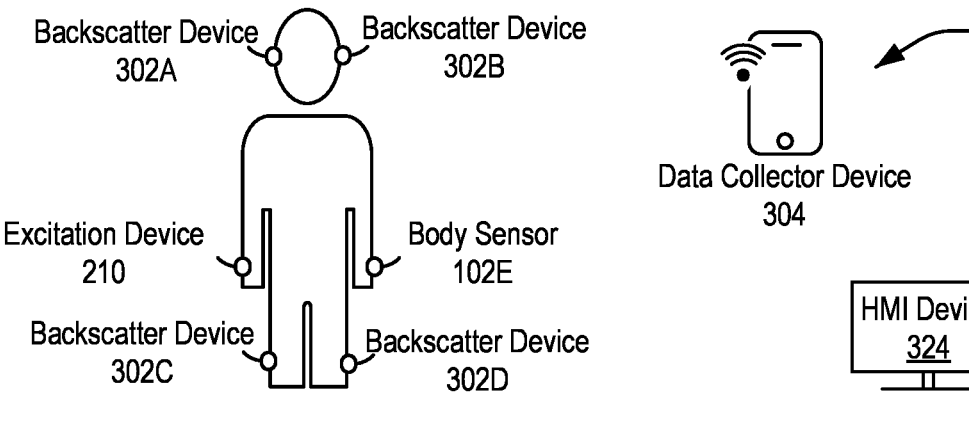
FIG. 3B
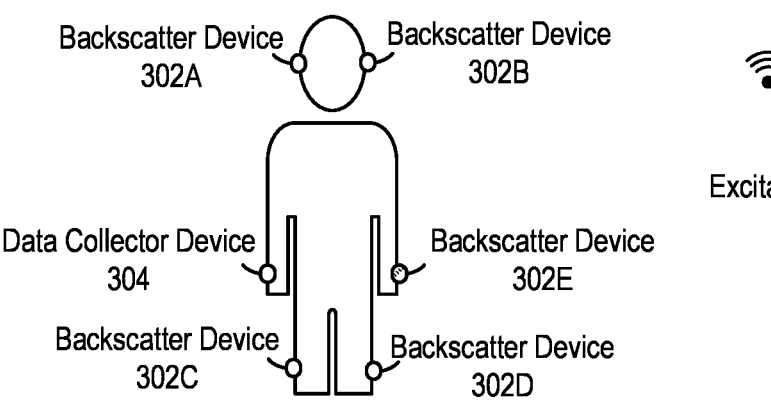
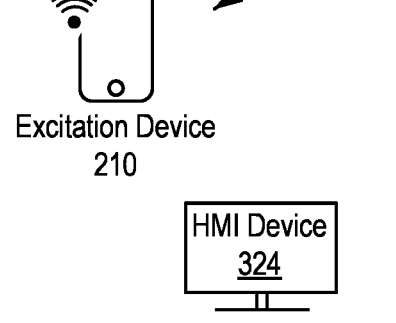
FIG. 3C

Backscatter Device
302

Data Collector Device
304

Excitation Device
306

General Sensor Device
307

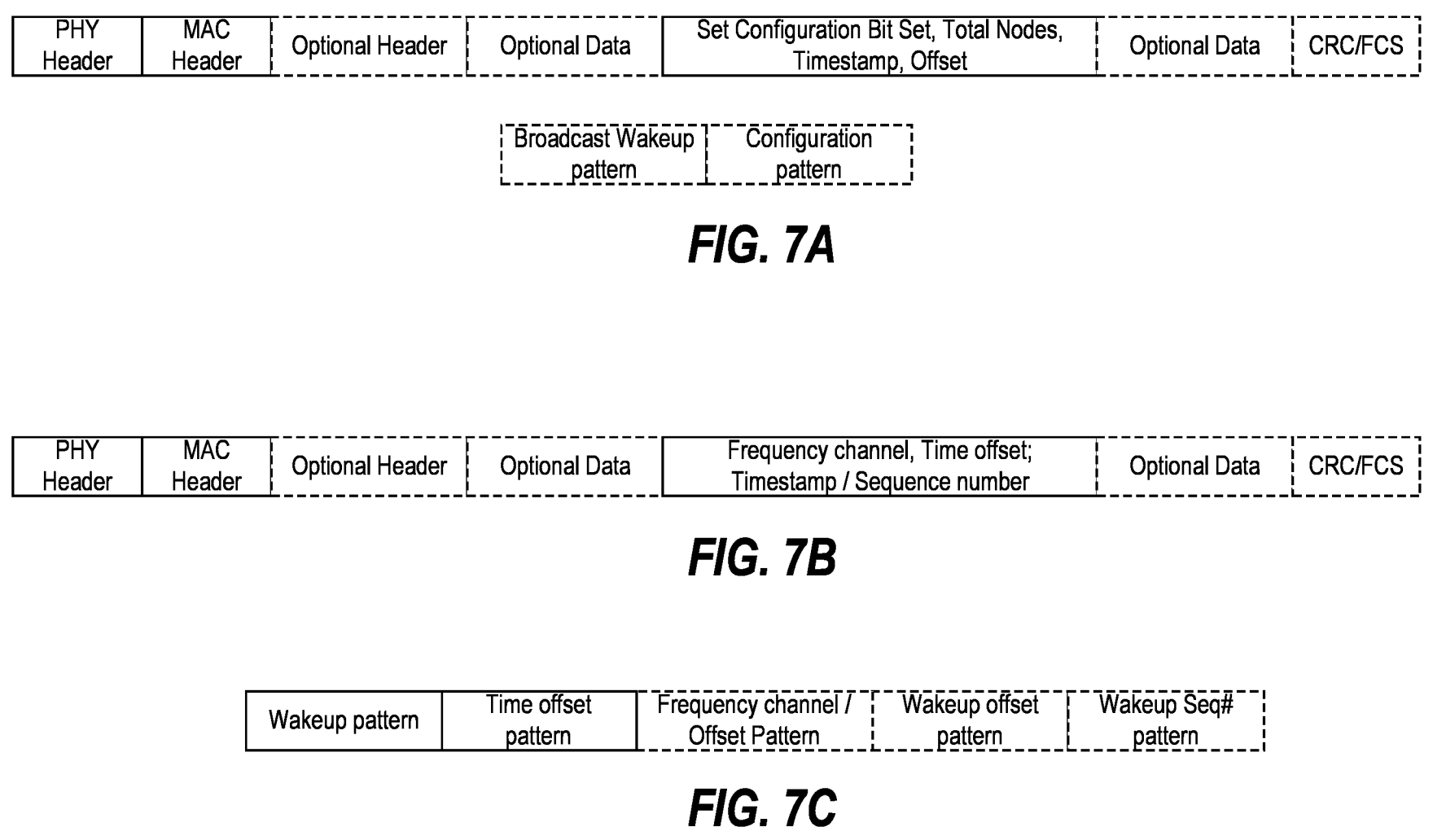

| PHY Header | MAC Header | Optional Header | Optional Data | Set Configuration Bit Set, Total Nodes, Timestamp, Offset | Optional Data | CRC/FCS |
|---|---|---|---|---|---|---|

| Broadcast Wakeup pattern | Configuration pattern |
|---|---|

FIG. 7A

| PHY Header | MAC Header | Optional Header | Optional Data | Frequency channel, Time offset; Timestamp / Sequence number | Optional Data | CRC/FCS |
|---|---|---|---|---|---|---|

FIG. 7B

| Wakeup pattern | Time offset pattern | Frequency channel / Offset Pattern | Frequency channel / Wakeup offset pattern | Wakeup offset pattern | Wakeup Seq# pattern |
|---|---|---|---|---|---|

FIG. 7C

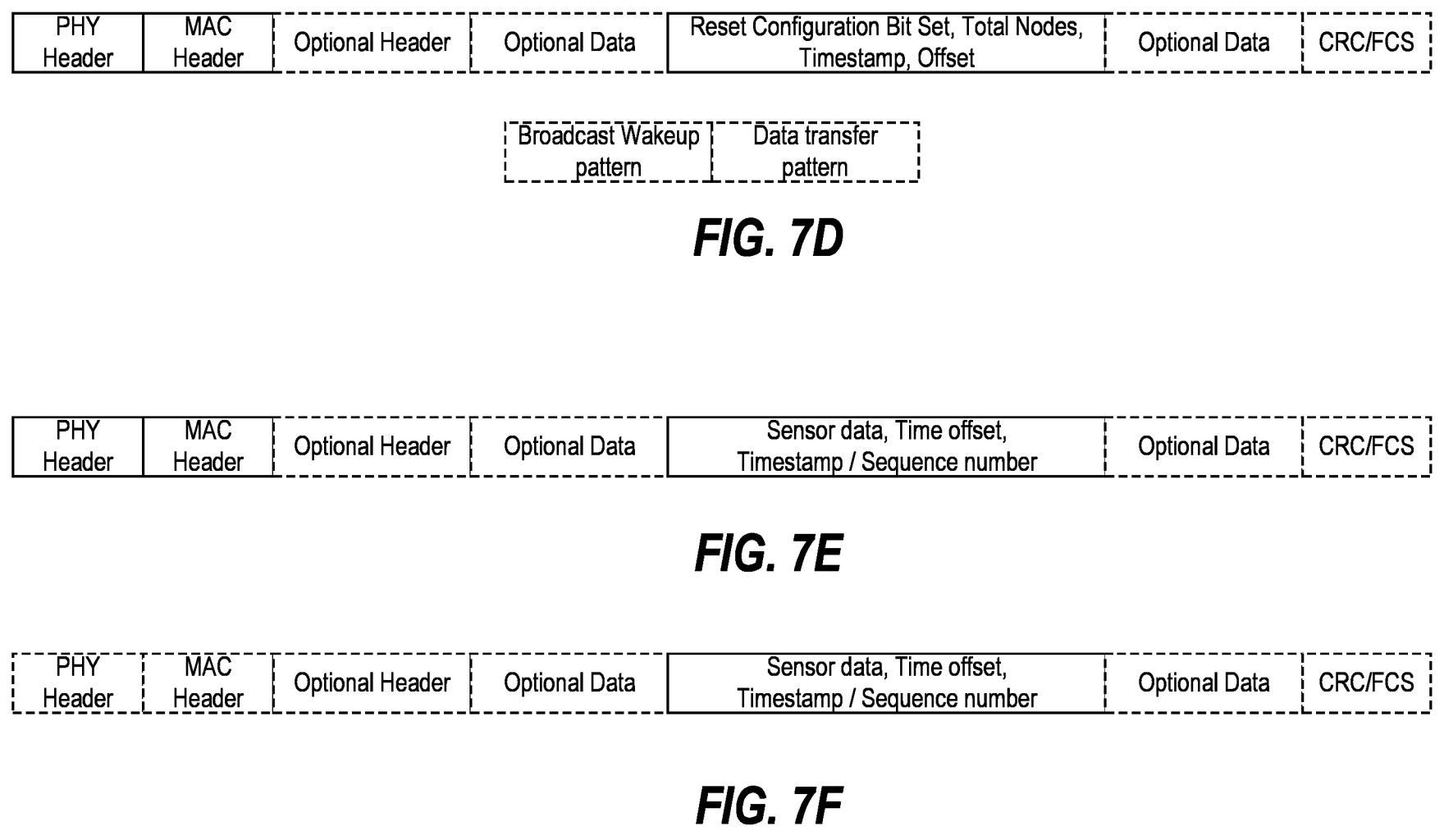

| PHY Header | MAC Header | Optional Header | Optional Data | Reset Configuration Bit Set, Total Nodes, Timestamp, Offset | Optional Data | CRC/FCS |
|---|---|---|---|---|---|---|

Broadcast Wakeup pattern | Data transfer pattern

FIG. 7D

| PHY Header | MAC Header | Optional Header | Optional Data | Sensor data, Time offset, Timestamp / Sequence number | Optional Data | CRC/FCS |
|---|---|---|---|---|---|---|

FIG. 7E

| PHY Header | MAC Header | Optional Header | Optional Data | Sensor data, Time offset, Timestamp / Sequence number | Optional Data | CRC/FCS |
|---|---|---|---|---|---|---|

FIG. 7F

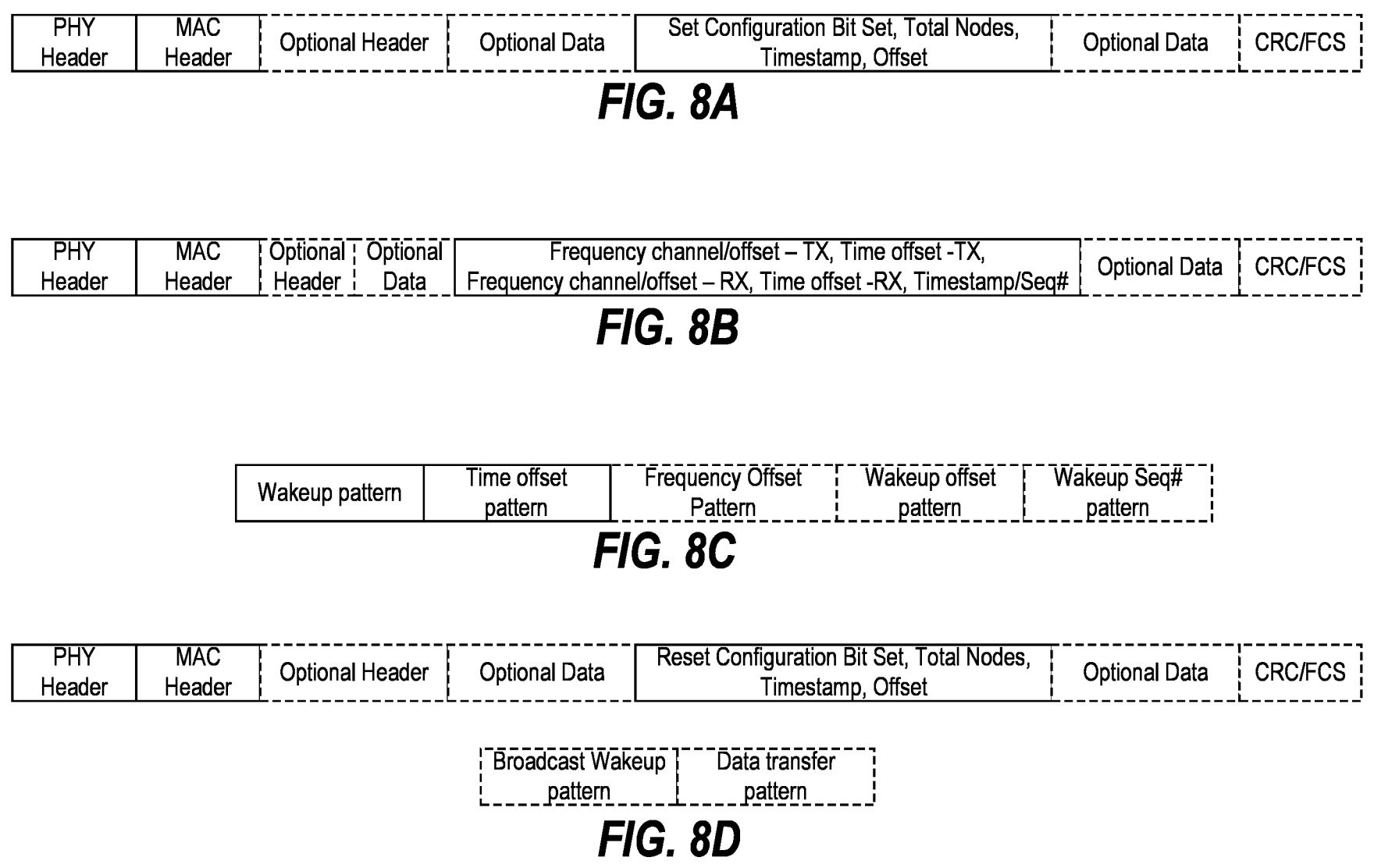

| PHY Header | MAC Header | Optional Header | Set Configuration Bit Set, Total Nodes, Timestamp, Offset | Optional Data | CRC/FCS |
|---|---|---|---|---|---|

FIG. 8A

| PHY Header | MAC Header | Optional Header | Optional Data | Frequency channel/offset – TX, Time offset -TX, Frequency channel/offset – RX, Time offset -RX, Timestamp/Seq# | Optional Data | CRC/FCS |
|---|---|---|---|---|---|---|

FIG. 8B

| Wakeup pattern | Time offset pattern | Frequency Offset Pattern | Wakeup offset pattern | Wakeup Seq# pattern |
|---|---|---|---|---|

FIG. 8C

| PHY Header | MAC Header | Optional Header | Reset Configuration Bit Set, Total Nodes, Timestamp, Offset | Optional Data | CRC/FCS |
|---|---|---|---|---|---|

| Broadcast Wakeup pattern | Data transfer pattern |
|---|---|

FIG. 8D

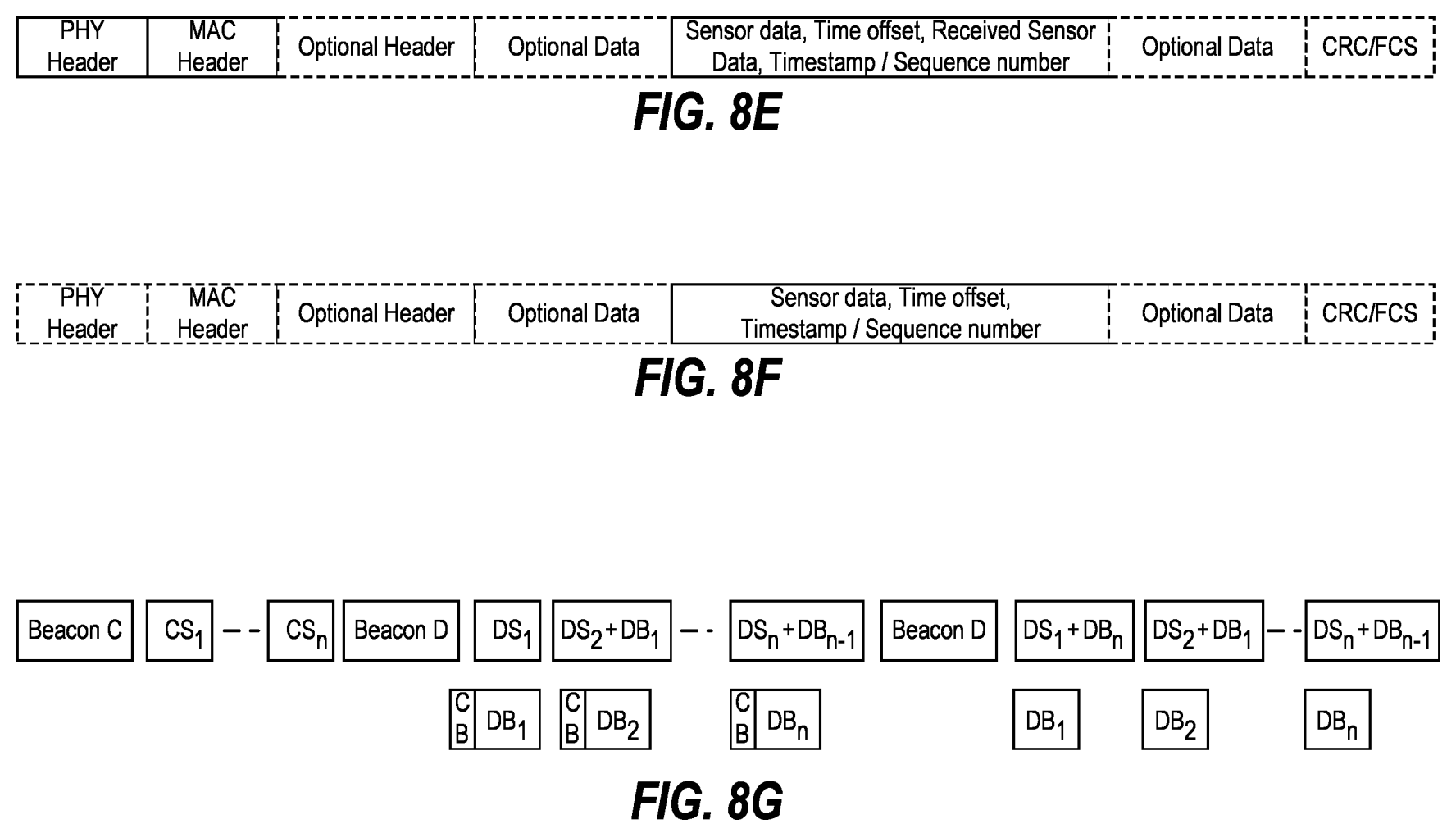

| PHY Header | MAC Header | Optional Header | Optional Data | Sensor data, Time offset, Received Sensor Data, Timestamp / Sequence number | CRC/FCS |
|---|---|---|---|---|---|

*FIG. 8E*

| PHY Header | MAC Header | Optional Header | Optional Data | Sensor data, Time offset, Timestamp / Sequence number | CRC/FCS |
|---|---|---|---|---|---|

*FIG. 8F*

Beacon C | $CS_1$ | -- | $CS_n$ | -- | Beacon D | $DS_1$ | $DS_2 + DB_1$ | -- | $DS_n + DB_{n-1}$ | Beacon D | $DS_1 + DB_n$ | $DS_2 + DB_1$ | -- | $DS_n + DB_{n-1}$ $\begin{array}{c} C \\ B \end{array}$ $DB_1$ | $\begin{array}{c} C \\ B \end{array}$ $DB_2$ | $\begin{array}{c} C \\ B \end{array}$ $DB_n$ | $DB_1$ | $DB_2$ | $DB_n$

Processor

1008

Network Device

1010

Output Device

1012

Input Device

1006

Storage

Computing Device
1002

BODY AREA NETWORK WITH BISTATIC WIRELESS BACKSCATTERING DEVICES

TECHNICAL FIELD

Aspects of the disclosure relate to the configuration and operation of body area networks to capture sensor data about a user.

BACKGROUND

A body area network involves communication between at least one body worn device and other body worn or external devices. Most applications fall into either personalized applications or medical applications. Personalized applications may include health, wellness, fitness, sports, etc., while medical applications have more stringent requirements with regards to data security, interoperability, and performance. To address body area network requirements for medical applications, there are several standardization efforts including the Institute of Electrical and Electronics Engineer (IEEE) 802.15.6 standard. On the other hand, for personalized applications there are no specific standards.

SUMMARY

In one or more illustrative examples, a method for configuring and utilizing a body area network (BAN), includes in a configuration phase, sending configuration messages for scheduling a plurality of backscatter devices such that during a data collection phase each of the plurality of backscatter devices is configured to backscatter from an excitation signal in an individually-assigned time slot; and in the data collection phase, receiving, to a data collector device from the plurality of backscatter devices, sensor data messages including sensor data from the backscatter devices, the sensor data messages being scheduled according to the configuration phase.

In one or more illustrative examples, a system for configuring and utilizing a BAN includes a plurality of backscatter devices and a data collector device. In a configuration phase, the plurality of backscatter devices are configured to receive configuration messages for scheduling transmissions of the plurality of backscatter devices, such that during a data collection phase each of the plurality of backscatter devices is configured to transmit in an individually-assigned time slot. In the data collection phase, the data collector device is configured to receive, from the plurality of backscatter devices, sensor data messages including sensor data from the backscatter devices, the sensor data messages being scheduled according to the configuration phase.

BRIEF DESCRIPTION OF THE DRAWINGS

FIG. 3A illustrates a first body area network architecture, in which backscatter devices, a data collector device, and an excitation device are located on the body;

FIG. 3B illustrates a second body area network architecture, in which backscatter devices and the excitation device are on body, while the data collector device is an external device;

FIG. 3C illustrates a third body area network architecture in which backscatter devices and the data collector device are on body, while the excitation device is an external device;

FIG. 7A illustrates an example of a configuration beacon message (Beacon C);

FIG. 7B illustrates an example of a configure sensor (CS) message;

FIG. 7C illustrates an example of a configure backscatter (CB) message for backscatter devices;

FIG. 7D illustrates an example of a data period beacon message (Beacon D);

FIG. 7E illustrates an example of a sensor data message (DS);

FIG. 7F illustrates an example of a backscatter data message (DB);

FIG. 8A illustrates an example of a configuration Beacon C message for the architecture including data aggregation;

FIG. 8B illustrates an example of a CS message for the architecture including data aggregation;

FIG. 8C illustrates an example of a CB for backscatter devices for the architecture including data aggregation;

FIG. 8D illustrates an example of a Beacon D for the architecture including data aggregation;

FIG. 8E illustrates an example of a DS for the architecture including data aggregation;

FIG. 8F illustrates an example of a backscatter data message (DB) for the architecture including data aggregation;

FIG. 8G illustrates an example of periodic message scheduling for data transfer in a pipeline enabled, single receiver architecture with data aggregation;

DETAILED DESCRIPTION

As required, detailed embodiments of the present invention are disclosed herein; however, it is to be understood that the disclosed embodiments are merely exemplary of the invention that may be embodied in various and alternative forms. The figures are not necessarily to scale; some features may be exaggerated or minimized to show details of particular components. Therefore, specific structural and functional details disclosed herein are not to be interpreted as limiting, but merely as a representative basis for teaching one skilled in the art to variously employ the present invention.

Aspects of the disclosure relate to providing low power wireless connectivity among body worn devices, as well as with non-body worn devices in communication with the body worn devices. Several applications such as health, wellness, fitness, sports, etc., require a user to wear one or more sensor devices on the body to provide sensor data. This sensor data may be utilized to measure and optimize properties such as posture correction, exercise monitoring/recommendation, sports performance, etc.

Body worn sensors are usually battery powered for optimal user experience and, in some cases, required by application itself. Because body worn devices are generally battery powered, a tradeoff between power consumption and data rate/latency remains a key challenge. Hence, low power consumption is very important, along with satisfying data rate, latency, and interoperability requirements.

Given that most applications require communication over a small distance, in this disclosure, sensors with wireless backscatter communication capability are used. Such devices may lead to an order of magnitude power savings for wireless communication compared to transceiver-based solutions. The management of several backscatter sensors and supporting quality of service requirement of the application is non-trivial. Further aspects of the disclosure present methods to support those requirements.

Figure 1:
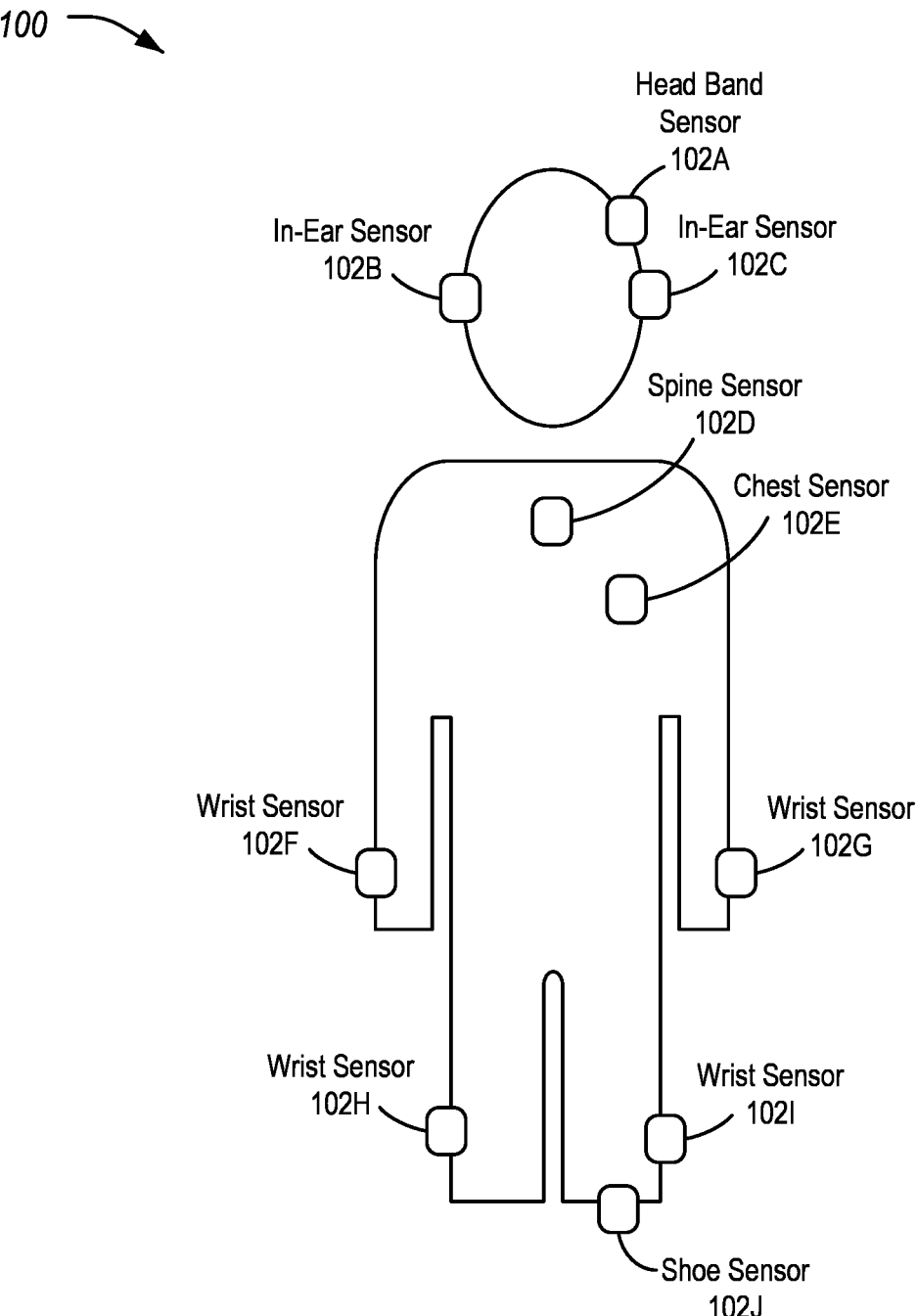
FIG. 1 illustrates an example of an application where a person is wearing several sensors on the body.

FIG. 1 represents an application in which a user is wearing several sensors 102 on the body. These sensors 102 may be placed directly on human body (e.g., with or without a casing) or may be embedded in body worn objects such as clothing, shoes, etc. As shown, the user is wearing a headband sensor 102A on the user's head. The user is also wearing in-ear sensors 102B, 102C in either ear. The user also has a spine sensor 102D located on the user's spine, and a chest sensor 102E located on the user's chest. The user also has wrist sensors 102F, 102G on each wrist and ankle sensors 102H, 102I on either ankle. The user also has a shoe sensor 102J in the user's shoe. It should be noted that these sensors 102 are merely examples, and more, fewer, or differently located sensors 102 may be used. At least one of those sensors 102 may utilize backscatter communication. Backscatter communication may be monostatic, bistatic, or interoperable.

Figure 2A:
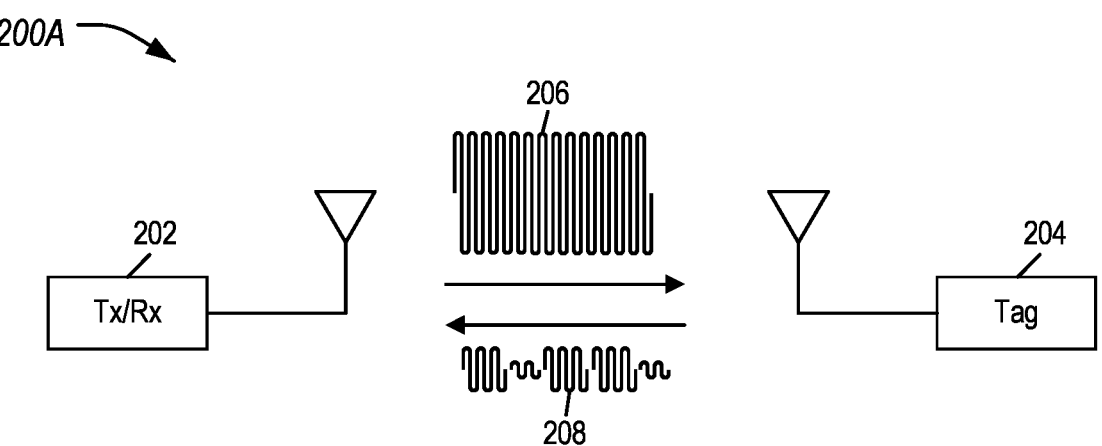
FIG. 2A illustrates an example of a monostatic backscatter configuration.

FIG. 2A illustrates an example 200A of a monostatic backscatter configuration. Such a configuration includes two main components: a transceiver device 202 denoted here as Tx/Rx and a tag 204. The transceiver device 202 may operate as a carrier emitter and may provide a radio frequency (RF) excitation signal 206 to activate the tag 204. The tag 204 may modulate the received excitation signal 206 to provide a backscatter signal 208 reflected back from the tag 204. The transceiver device 202 may then receive the backscatter signal 208.

Figure 2B:
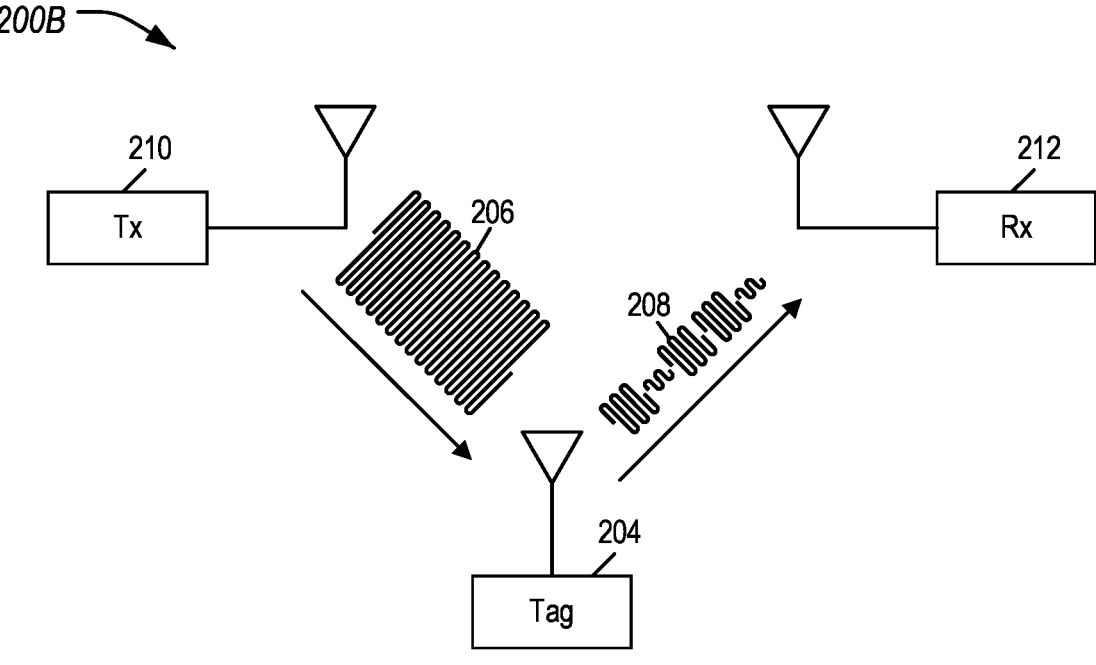
FIG. 2B illustrates an example of a bistatic backscatter configuration.

FIG. 2B illustrates an example 200B of a bistatic backscatter configuration. Such a configuration includes three main components: a transmitter device 210 denoted here as Tx, a tag 204, and a receiver device 212 denoted here as Rx. In such an example, the transmitter and receiver functions of the transceiver device 202 are separated. Here, the transmitter device 210 may operate as the carrier emitter and may provide the excitation signal 206 to activate the tag 204. The excitation signal 206 may be a continuous wave (CW) or a modulated signal of standard technologies such as BLUETOOTH low energy (BLE), Wi-Fi, 802.15.4 or any other proprietary wireless protocol. The tag 204 may modulate the excitation signal 206 to provide the backscatter signal 208 reflected back from the tag 204. The receiver device 212 may then receive the backscatter signal 208.

Backscatter devices may be active or passive. Active devices may have their own power source and can collect sensor data as needed. Passive sensors, on the other hand, may derive their power from an excitation signal 206 and therefore collect data only when such an excitation signal 206 is present. Single device backscatters have been proposed for body implant, eatable pills, and body sensors. Instead of RF energy, on-body devices or implants may also make use of magnetic energy (e.g., inductive coupling) for both data and power transfer.

During a backscattering event, the RF data transfer may be performed via backscattering only, and hence, may differ from a more traditional passive radio frequency identification (RFID) based solution which may transfer power and energy as well. As another distinction, the transmitter and receiver need not be co-located as in traditional RFIDs (either active or passive). This lack of co-location may require additional power efficient communication mechanisms between transmitters and receivers for achieving time synchronization and for configuring system/protocol parameters.

The disclosed approach focuses on backscatter node performance and system capacity. Energy scavenging from ambience in general may be insufficient for high data rate applications, so dedicated methods may be pursed instead. Out of the dedicated methods, non-radiative inductive coupling (e.g., in the range of a few centimeters) and non-radiative magnetic resonance coupling (e.g., in the range of a few tens of centimeters) may be considered safe for human tissue, which is important consideration for human body worn devices. Given that the charging range of these safe power harvesting methods is not enough for some intended use cases, instead the focus may be placed on optimizing data transfer and system capacity while optimizing power efficient communication.

The sensors 102 may be powered by a power source such as a super-capacitor or a battery. In some cases, the sensors 102 may scavenge energy from ambient conditions. It should be noted that various wireless charging methods may be utilized during usage of the sensor 102 devices on the human body. After the usage, the sensors 102 may be recharged or the batteries replaced.

FIGS. 3A-3C illustrate examples of a BAN 300 system architectures. FIG. 3A illustrates a first body area network 300A architecture, in which backscatter devices 302A-D, a data collector device 304, and an excitation device 306 are located on the body. FIG. 3B illustrates a second body area network 300B architecture, in which backscatter devices 302A-E and the excitation device 306 are on body, while the data collector device 304 is an external device. FIG. 3C illustrates a third body area network 300C architecture, in which backscatter devices 302A-E and the data collector device 304 are on body, while the excitation device 306 is an external device.

Figure 3D:
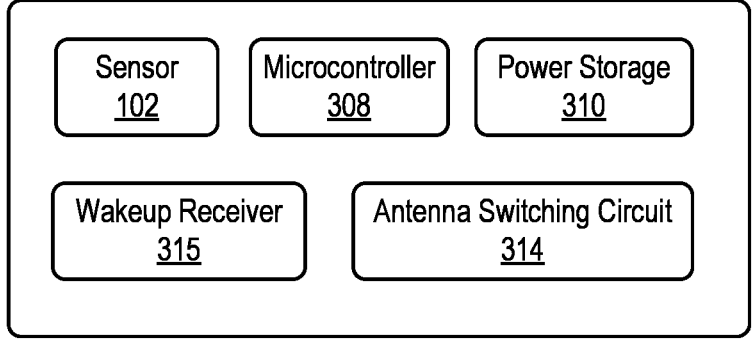
FIG. 3D illustrates further aspects of an example backscatter device.

FIG. 3D illustrates further aspects of an example backscatter device 302. As shown, the backscatter device 302 may include at least one sensor 102, a microcontroller 308 including a microprocessor, memory and I/O to connect with other peripherals, a power storage 310, an antenna switching circuit 314, and (optionally) a wakeup circuit 315. The sensors 102 may include inertial measurement units (IMUs) (such as an accelerometer or a gyroscope), a pressure sensor, an optical sensor, etc.

The microcontroller 308 may be utilized to generate a baseband signal and process sensor data. In some example, the backscatter device 302 may include a separate custom application specific integrated circuit (ASIC) for generating the baseband signal. Additionally, the sensors 102, microcontroller 308, and other components of the backscatter device 302 may be separate chips or packaged in one module.

The backscatter device 302 may be powered by the power storage 310. The power storage 310 may be a normal battery, a super capacitor, or a rechargeable battery. For rechargeable power options, the device may additionally utilize wired, wireless charging or ambient charging, power harvesting from kinetic energy, etc.

The backscatter device 302 may optionally include a wakeup circuit 315 configured to allow the backscatter device 302 to efficiently receive and understand wakeup signals. The backscatter device 302 may include an envelope detector to cause the backscatter device 302 to wake up only when signal is received above a given threshold. The wakeup signal may be provided using a simple On-Off Keying. One such implementation utilizes Manchester coded 125 kHz waveform.

The backscatter device 302 may also include a pattern correlator to wake up only when message is addressed to the transmit-only node by utilizing a unique pattern for each backscatter device 302. The backscatter device 302 may also employ machine learning and advance signal processing techniques to process application-specific data directly as derived from sensors 102, such as step counting, personalized fitness tracking, swim analytics, pedestrian always-on position tracking, etc. The backscatter device 302 may also include additional human machine interface (HMI) components, such as light emitting diodes (LEDs), haptics, etc., for providing user feedback.

The antenna switching circuit 314 may allow the backscatter device 302 to switch between receiving wakeup messages and modulating the excitation signal 206. The wakeup signal may be provided using a simple On-Off Keying. One such implementation utilizes Manchester coded 125 kHz waveform. The transmitted data packet signal may be of standard technologies such as BLE, Wi-Fi, IEEE 802.15.4, 5G reduced capacity, or any other proprietary wireless protocol. The backscatter device 302 may optionally utilize wakeup circuitry comprising an envelope detector, at a minimum, to wake up only when signal is above a given threshold. The backscatter device 302 may also include a pattern correlator to wake up only when message is addressed to the backscatter node by utilizing a unique pattern for each backscatter device 302.

When the antenna switching circuit 314 is in wakeup mode, the backscatter device 302 may be configured to listen for wakeup messages. When the antenna switching circuit 314 is in transmit mode, the backscatter device 302 may adjust received excitation signal 206 to generate the backscatter signal 208 to transmit information. The backscatter device 302 may also employ machine learning and advance signal processing techniques to process application-specific data directly as derived from sensors 102, such as step counting, personalized fitness tracking, swim analytics, pedestrian always-on position tracking, etc. The backscatter device 302 may also include additional HMI components, such as LEDs, haptics, etc., for providing user feedback.

Figure 3E:
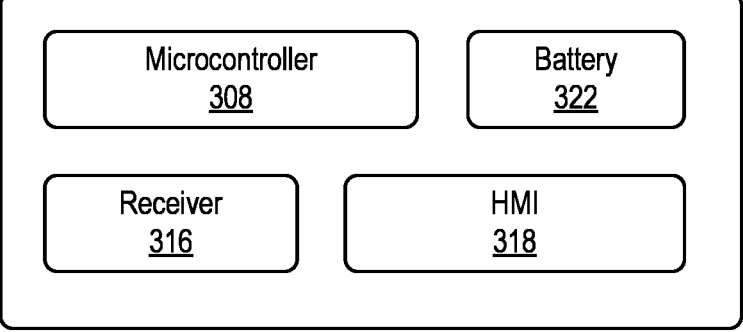
FIG. 3E illustrates further aspects of an example data collector device.

FIG. 3E illustrates further aspects of an example data collector device 304. The devices in the BAN 300 may take on various roles. The BAN 300 with backscatter devices 302 includes at least three main devices: at least one backscatter device 302, a data collector devices 304 configured to operate as a receiver of the transmissions from the sensor 102, and an excitation device 306.

The data collector device 304 may be placed on the body in some examples, but off the body in others. The data collector device 304 may be used to receive and aggregate data from multiple backscatter devices 302. The data collector device 304 may include a wireless receiver 316 to receive the transmitted backscatter data. In some implementations the wireless receiver 316 may be a transceiver 320 with send capability in addition to reception capability. The wireless receiver 316 may use the same wireless technology as the backscatter devices 302 and/or as other on-body general sensor devices 307 which use a transceiver 320. In addition to the wireless receiver 316 using same wireless technology as the backscatter devices 302, the wireless receiver 316 may also support additional wireless technologies such as Wi-Fi, BLE, IEEE 802.15.4, cellular, etc., to allow the data collector device 304 to communicate with additional HMI devices 324 such as televisions, display screens, or tablet computing devices.

For an optimal or immersive user experience, the data collector device 304 may include an HMI 318 to provide for user feedback. The data collector device 304 may also include a microcontroller 308 to aggregate and process sensor data for displaying or forwarding to the HMI devices 324. The data collector device 304 itself may be battery powered and may employ a rechargeable battery 322 which may be charged via wired or wireless means.

Figure 3F:
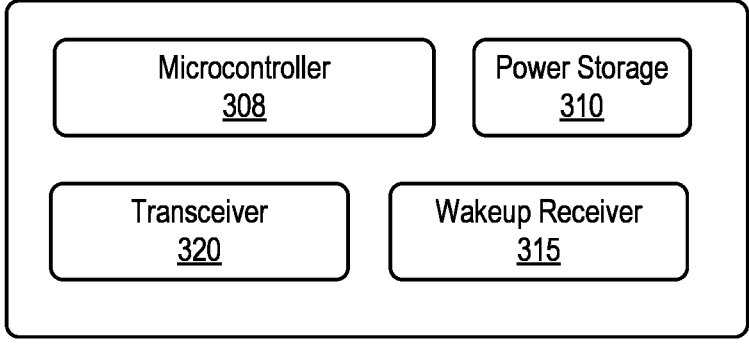
FIG. 3F illustrates further aspects of an example excitation device.
Figure 3G:
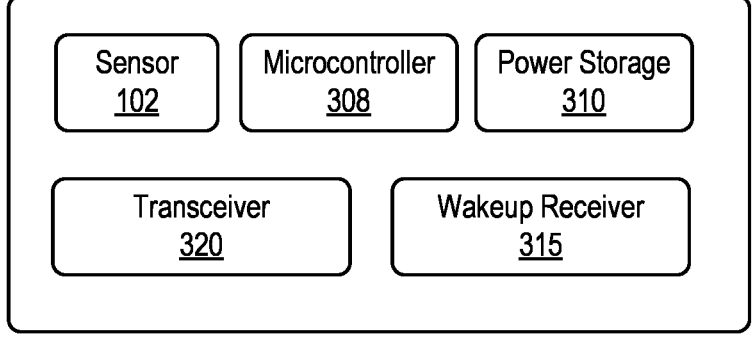
FIG. 3G illustrates further aspects of an example general sensor device.

FIGS. 3F-3G collectively illustrates further aspects of an example excitation device 306 and an example general sensor device 307. Similar to the backscatter device 302, the excitation device 306 may include a microcontroller 308 including a microprocessor, memory and I/O to connect with other peripherals, and a power storage 310. The excitation device 306 may be configured to provide the excitation signal 206.

In some examples, a general sensor device 307 may include the components of the excitation device 306 and also be configured to include a transceiver 320 to provide sensor signals based on its at least one sensor 102 (if so equipped).

The HMI devices 324 may also be configured to send the excitation signals 206. The HMI devices 324 or data collector devices 304 may also be configured, in other examples, to generate the excitation signals 206 and/or to generate wakeup signals to configure the devices.

The BAN 300 may collectively enable logging and/or analyzing of data from the sensors 102 for various applications. These applications may include, as some non-limiting examples: body motion capture application for orientation tracking like Yoga or curvature tracking such as running; posture correction and balancing; daily activities such as walking, running, biking, sleeping, etc.; fitness activities such as (full body) workouts, exercises, etc.; wellbeing activities such as yoga, dancing, meditation, etc.; sports activities such as soccer, boxing, basketball, cricket, badminton, tennis, table tennis, golf swing, swimming, etc.; and/or custom gestures such as pet activities (scratching), accessories (ring), skateboard, smartphone photo/QR-code scan, etc.

Figure 4:
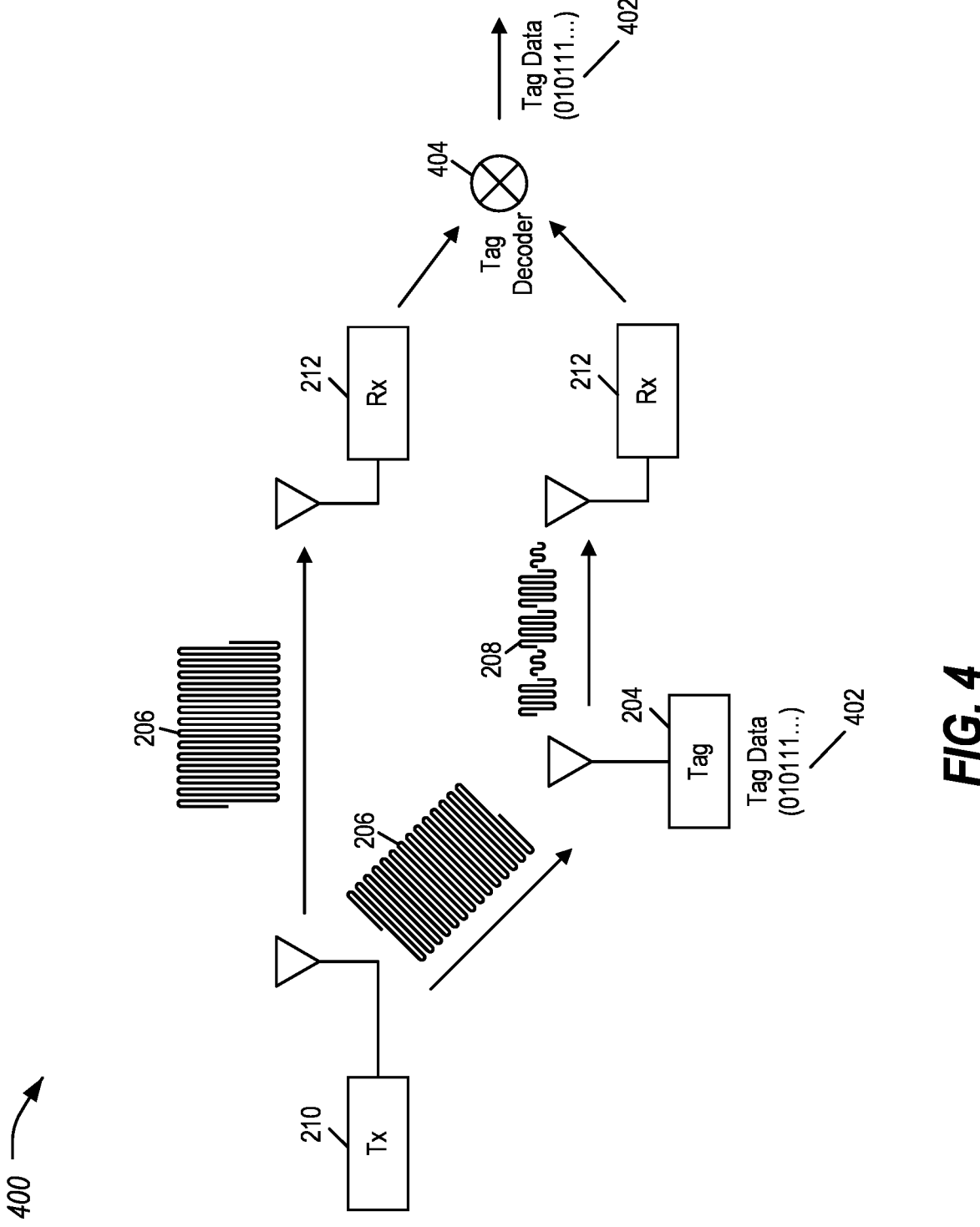
FIG. 4 illustrates an example mechanism of backscatter communication.

FIG. 4 illustrates an example mechanism 400 of backscatter communication. As shown, the backscatter device 302 may transmit in presence of the excitation signal 206. The excitation signal 206 may be a CW signal with a given center frequency, or may be a modulated signal of standard RF technology such as Bluetooth Low Energy, 802.15.4 based protocol (such as ZigBee, Thread, etc.), Wi-Fi, etc. The backscatter signal 208 is then one of these standard wireless technologies such as BLE, Wi-Fi, 802.15.4 based or any proprietary modulated signal. The backscatter signals 208 do not have any frequency radio components needed for carrier wave generation and hence depend on the excitation signal 206. However, this design also results in low power operation as the backscatter devices 302 modulate the excitation signal 206 as per receiver device 212 requirements.

As shown, the transmitter device 210 broadcasts the excitation signal 206. This excitation signal 206 is received by a receiver device 212. Also, the excitation signal 206 excited a tag 204 which thereby produces a backscatter signal 208. The excitation signal 206 may be any wireless signal generated using a set of known codewords from a fixed codebook. For example, Bluetooth uses frequency shift keying (FSK) modulation and has two codewords in its codebook: it transmits a tone at one frequency to send data one, and a different frequency to send zero. Similarly, WiFi and ZigBee also have finite sets of codewords that vary in combinations of phase, amplitude or frequency. To do codeword translation, the tag 204 transforms the excitation signal 206 codeword into another valid codeword in the same codebook during backscattering. This is done by modifying one or more of the amplitude, phase, and frequency of the excitation signal 206. The specific translation depends on the data that the tag 204 wants to communicate and the type of the excitation signal 206. Because the codeword in the backscattered signal is a valid codeword from the same codebook as the original excitation signal 206, this backscatter signal 208 may similarly be received by a receiver device 212. Both the excitation signal 206 and the backscatter signal 208 are then provided to a tag decoder 404. The tag decoder 404 may determine the backscatter signals 208 based on its knowledge of the excitation signal 206.

The mechanism 400 shown in FIG. 4 may be acceptable for a single backscatter device 302 within the environment of the BAN 300, such as in the case of a medical implant with a limited range. However, in BANs 300 that have several backscatter devices 302 in the environment, either on single user or multiple users nearby, then all the backscatter devices 302 in the vicinity may respond at once to the excitation signals 206. To decipher the individual messages from the backscatter devices 302, the BAN 300 may, for example, shift those respective responses to different frequency channels, which will also require many receivers on different channels to receive those messages. Such an approach would add cost and at the same time limit system capacity (e.g., limit the total number of backscatter devices 302 in the vicinity) to a maximum number of frequency channels onto which the modulated signal can be shifted. At the same time, if the receiver hops between different frequency channels to receive messages from these backscatter devices 302, then energy of the backscatter devices 302 may be wasted for the messages which are not received. Further, as these backscatter devices 302 may lack receiver, the backscatter devices 302 may be unable to receive feedback and may keep on transmitting whether their messages are received or not. Therefore, additional methods may be utilized to arbitrate the wireless channel and to avoid wasting the energy of the backscatter devices 302.

Figures 5, 6:
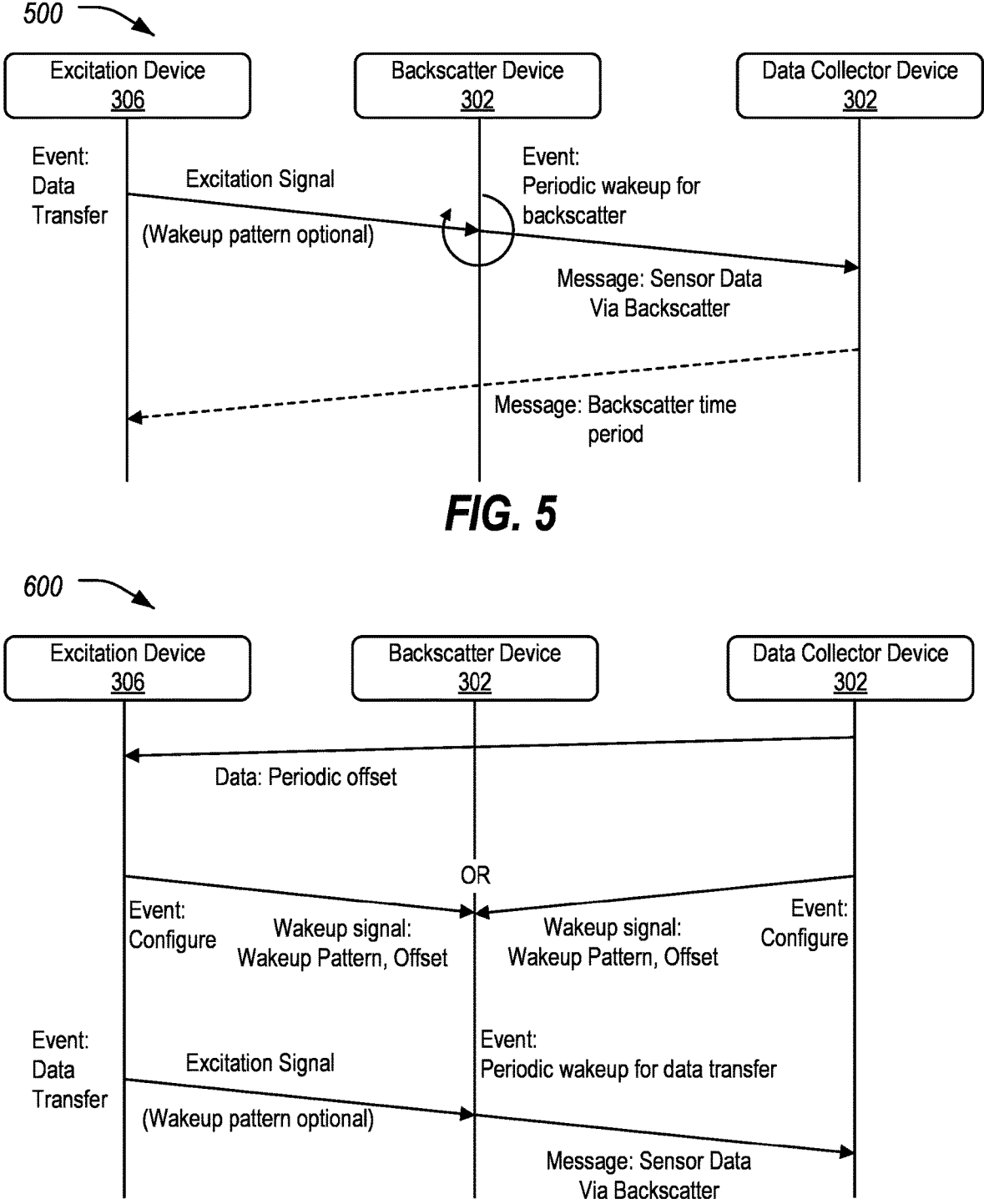
FIG. 5 illustrates an example of a predetermined periodic wakeup of a backscatter device.
FIG. 6 illustrates an example of an optimized periodic wakeup using channel arbitration techniques.

Referring to FIG. 5, an example of a predetermined periodic wakeup of a backscatter device 302 is illustrated. The example shown in FIG. 5 assumes a constant excitation signal 206 at the outset of the process, for example until the data collector device 304 synchronizes with the transmission pattern of the backscatter device 302. The backscatter device 302 may transmit sensor data via backscatter responsive to expiration of a timer for transmission as shown.

For a periodic transmission approach, each backscatter device 302 may collect sensor data for a pre-determined period of time such that when the timer expires, the backscatter device 302 transmits the sensor data. The periodic interval time information may be included in the backscatter message, or the data collector device 304 may receive first few initial message from each backscatter device 302 to determine the periodic time interval for a given backscatter device 302. The data collector device 304 may then inform the excitation device 306 about the periodic time interval of the excitation signal 206 needed for the backscatter device 302 (e.g., denoted by the dotted message from the data collector device 304 in FIG. 5). The excitation device 306 may also send the excitation signal 206 as a combination of different frequencies, power levels, antennas (in case transmitter has multiple antennas) and based on the received signal quality of backscatter data. For instance, the data collector device 304 may create a whitelist of these parameters for each transmitter.

For a random transmission approach, each backscatter device 302 may collects data for a random period of time, such that once the timer expires the backscatter device 302 may backscatter the data along with a time interval for the next round of transmission. The data collector device 304 may inform the excitation device 306 about the next time interval for sending the excitation signal 206 for this backscatter device 302. Similar to the periodic example, the excitation signal 206 may be sent over combination of different frequencies, power levels, antennas (in case transmitter has multiple antennas) to allow the data collector device 304 to create whitelist combinations over time. In an alternative, the backscatter device 302 may also wake up randomly and decide whether to transmit based on a random probability (e.g., taken from a uniform distribution between 0 and 1). If the probability is above a predefined threshold, e.g., $1/n$ where n is total number of backscatter devices 302, then the backscatter device 302 may backscatter, otherwise the backscatter device 302 may not backscatter. Responsive to the backscatter device 302 determining not to backscatter, the backscatter device 302 may wait for a shorter random time again before calculating the probability for transmission. The method is similar to p persistent carrier sense multiple access (CSMA).

For a low power wakeup receiver approach, each of the backscatter devices 302 may be equipped with a wakeup circuit 315. The wakeup circuit 315 may trigger the backscatter device 302 to backscatter responsive to the excitation signal 206 exceeding a predefined threshold signal level. This may address the issue of transmitting to be performed only when the transmitter is within distance. With transmission power control, it can therefore be ensured that only backscatter devices 302 on the human body with the transmitter will wake up and backscatter. This approach may be acceptable if there is only a single backscatter device 302 on the body.

However, in case of many backscatter devices 302, an additional approach for channel arbitration may be desired to ensure that messages can be received from all of the backscatter devices 302. Otherwise, energy in transmitting may be wasted if those messages are ignored or overlap or are otherwise unable to be received. This channel arbitration may be performed in various ways, such as those indicated below. One of more of these channel arbitration approaches may be combined to further improve performance with multiple backscatter devices 302.

In one channel arbitration approach, each backscatter devices 302 may randomly decide whether to backscatter or not to backscatter (e.g., when the backscatter devices 302 has data to provide). backscatter devices 302 may not need to backscatter when it has no data to send, unless the time between last backscatter communication exceeds a pre-determined sending timeout. In that case, the backscatter devices 302 may still backscatter a message to indicate that the backscatter devices 302 is still alive.

In another channel arbitration approach, each backscatter devices 302 may backscatter on a different channel, so either at receiver we have multiple receivers (e.g., operating on different channels) or a software radio that can receive all backscatters messages simultaneously. Or the receiver may decide which backscatter device 302 to tune in. In this case, energy may be expended for backscatter devices 302 that are unnecessary to be listened to.

In another channel arbitration approach, a node identifier (ID) may be coded in the wakeup signal which is detected by the pattern correlator at the receiver. This may allow the indicated backscatter node to respond while the other back-scatter devices 302 ignore the wakeup message.

FIG. 6 illustrates an example of an optimized periodic wakeup using channel arbitration techniques. For instance, a time offset may be piggybacked in the wakeup pattern along with node ID to inform the backscatter device 302 about its time period for transmission. During normal transmission, the BAN 300 does not require to include a wakeup pattern, thereby reducing energy consumption and enhancing system capacity. To offset normal clock drifts, such configuration messages may be sent from time to time. This configuration message may be sent from either the device sending the excitation signal 206 or from the receiver itself.

Also as shown, the data collector device 304 may send a periodic offset to the excitation device 306. The excitation device 306 may then send a configure event to the backs-catter device 302, which may include a wakeup signal having a wakeup pattern and/or the periodic offset. In the alternative, the excitation device 306 may send the configure event to the backscatter device 302 which may include a wakeup signal having a wakeup pattern and/or the periodic offset. Responsive to the periodic wakeup for the data transfer occurring, the backscatter device 302 may send the message data via backscatter.

FIGS. 7A-7H illustrates aspects of a system protocol design and message formats including message scheduling. Two approaches are discussed: a no pipeline, single radio architecture and a pipeline enabled, dual radio architecture.

In the no pipeline, single radio architectures, the data collector device 304 is assumed to have only one radio and hence all devices are scheduled sequentially. Initially a configuration phase is performed where the controller device sends the Beacon C (configuration) messages to configure at least the backscatter devices 302. This instructs the excita-tion device 306 to broadcast a wakeup pattern followed by the configuration Beacon C message. During the configu-ration phase, each of the general sensor devices 307 and backscatter devices 302 is scheduled, such that during a data collection phase each of them can transmit in their indi-vidual assigned/calculated time slots.

In the pipeline enabled, dual radio architecture, two radios are assumed for reception at the data collector device 304: one for general sensor devices 307 and one for backscatter devices 302. The advantage of such an architecture is that when general sensor devices 307 are being configured, backscatter devices 302 may be configured in parallel (i.e., pipelined) on a separate channel. Another advantage is a shorter duration of the data collection phase. Here it is not required to send a separate excitation signal 206, as the data transferred by the general sensor devices 307 may be used as the excitation signal 206 by the backscatter devices 302 to backscatter their different signal using codeword transla-tion as explained herein. Thus, the system capacity can be doubled at a cost of one additional radio at the receiver. An alternate setup may utilize a collector for collecting data from all general sensor devices 307 with an HMI/display device from all backscatter devices 302 (or vice versa). The device which receives the data may thereby have both the original data from the sensors and also the coded data from the backscatter signals 208 which may be used to decipher the backscatter message.

The key messages for these architectures may include Beacon C messages, configuration messages, Beacon D (data) messages, and data collection messages.

FIG. 7A illustrates an example of a configuration beacon message (Beacon C). As shown, the Beacon C message may include a physical header, a media access control (MAC) header, and/or other optional headers or optional data for the physical layer and/or protocol being used. Depending on the protocol being used, the Beacon C message may also include data correction checks such as cyclic redundancy check (CRC) or frame check sequence (FCS). Further, the Beacon C message may also be encrypted with the methods agreed upon during pairing processes of respective wireless tech-nologies.

The payload of the Beacon C message may include information for use by the excitation device 306 in initiating system configuration. For instance, to identify the message as being the Beacon C message, the Beacon C message may include a configuration bit set to '1' (or another value denoting the Beacon C message is a configuration message). Further, the Beacon C message may include a timestamp to synchronize system clocks of network devices and to avoid replay attacks. The Beacon C message may further include a total number of devices (e.g., the general sensor devices 307 and the backscatter devices 302) and optionally an offset value to indicate the beginning of data collection phase.

Responsive to receiving the Beacon C message, the excitation device 306 or other device responsible for gen-erating the excitation signal 206, if any, may proceed to configure each of the backscatter devices 302. The excitation device 306 or other responsive device may also send a system broadcast wakeup pattern including a pattern to indicate beginning of configuration cycle. This could be used by the other devices to synchronize their clocks.

FIG. 7B illustrates an example of a configure sensor (CS) message for general sensor devices 307. These CS messages may be individually sent to general sensor devices 307 to inform the general sensor devices 307 about the frequency channel to be used for data transfer and time offset (with respect to reception of data collection cycle beacon mes-sage). When number of devices is small, there could also be one large beacon message with data for all sensors 102. The configuration message may also include its own timestamp or sequence number, e.g., to avoid replay attacks.

FIG. 7C illustrates an example of a configure backscatter (CB) message for backscatter devices 302. For the backs-catter devices 302, the wakeup signal may include an individual wakeup pattern for each backscatter device 302. This wakeup pattern may be appended with additional information, such as time offset pattern denoting, from reception of this message or reception of wakeup message, the configuration of data collection with the indicated broadcast pattern. In the first case, the message may also include periodic wakeup offset pattern. Additionally, the wakeup pattern may also be appended with frequency offset and/or a wakeup sequence number pattern (e.g., to avoid replay attacks on wakeup patterns).

The configuration of general sensor devices 307 and backscatter devices 302 may also occur in parallel when configuration of these two sets is done by two different devices, e.g., by data collector devices 304 and excitation devices 306, respectively, for pipelined architectures.

FIG. 7D illustrates an example of a data period beacon message (Beacon D). The Beacon D messages may be sent from controller to initiate data collection with configuration bit set to '0' or another value denoting the Beacon D message as a non-configuration message. The remainder of the format and content of the Beacon D messages may be similar to that in the configuration messages. The excitation device 306 may also send a system broadcast wakeup pattern including a pattern to indicate the beginning of a data transfer cycle. This may be used by devices to synchronize their clocks.

FIG. 7E illustrates an example of a sensor data message (DS). These sensor data messages may be sent from general sensor devices 307. During the data collection phase, each of the general sensor devices 307 transmits their data as per their assigned offsets to the data collector device 304.

FIG. 7F illustrates an example of a backscatter data message (DB). For the backscatter devices 302, the backscatter devices 302 wakeup periodically as well to transmit backscatter signal 208 while the excitation device 306 sends the excitation signal 206 continuously during the data collection phase. The excitation device 306 may also send the excitation signal 206 based on whitelist combination of frequency channel, power level, antenna, etc., as set by the receiver/collector/wakeup device during configuration phase. The backscatter data message could itself conform to standard protocol and hence can have its associated headers and data check bits. The devices may also include their time offsets values that could assist receiver/collector to initiate synchronization as needed.

Depending on application data rate requirements there could be gap between successive data collection cycles denoted by offset in data period beacon.

Figures 7G, 7H:
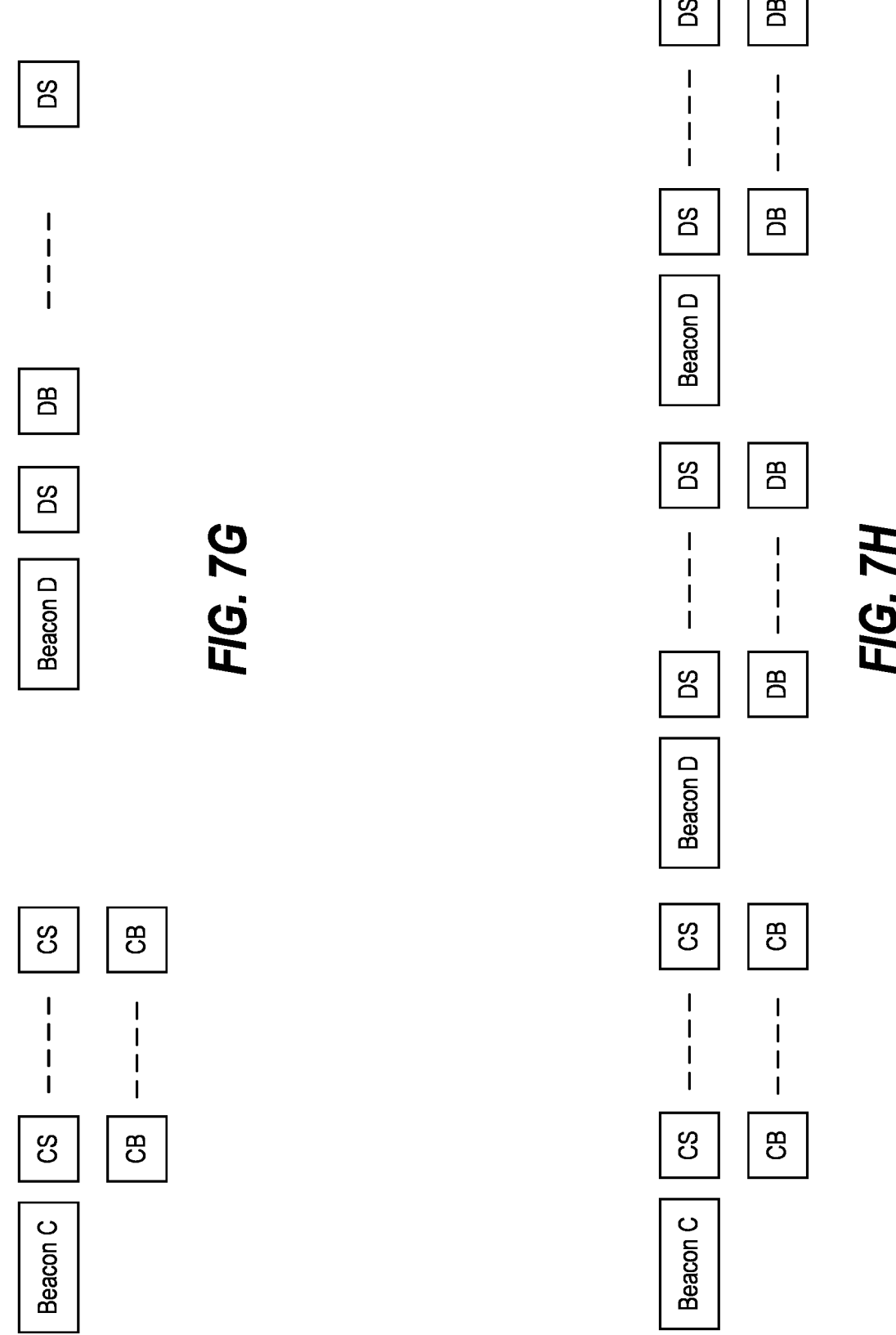
FIG. 7G illustrates an example of periodic message scheduling for data transfer in a no pipeline, single radio receiver architecture.
FIG. 7H illustrates an example of periodic message scheduling for data transfer in a pipeline enabled, two separate receivers/single receiver device with two radios architecture.

FIG. 7G illustrates an example of periodic message scheduling for data transfer in a no pipeline, single radio receiver architecture. As shown, in the configuration phase, Beacon C messages are sent (as shown in FIG. 7A) e.g., by a collector/receiver device, followed by CS messages (as shown in FIG. 7B). Another source, the excitation source, sends the CB messages (as shown in FIG. 7C). In doing so, the CS and CB messages may be sent concurrently and/or in an overlapping pattern on different frequency channels, speeding up the configuration phase. This pattern may be repeated (e.g., periodically). It should also be noted that the order of the Beacon C, CS, and CB messages is not relevant, and may be sent in orderings other than as shown. In the data phase, the Beacon D messages may be sent (as shown in FIG. 7D), followed by DS messages (as shown in FIG. 7E), followed by DB messages (as shown in FIG. 7F). This pattern may also be repeated (e.g., periodically). It should also be noted that the relative order of the Beacon D, DS, and DB messages may differ from that as shown.

FIG. 7H illustrates an example of periodic message scheduling for data transfer in a pipeline enabled, two separate receivers/single receiver device with two radios architecture. Here again, a first source (collector/receiver) sends the Beacon and CS messages, while another source (collector/receiver) sends the CB messages. Additionally, as two receivers or two radios are used, the first source sends the Beacon D and receives DS messages, while the second source receives the DB messages concurrently.

FIGS. 8A-8G and 9 illustrate an optimized pipeline architecture with data aggregation that may also be provided by the BAN 300. In this variation, the general sensor devices 307 may be scheduled for backscatter communication. In each data communication slot, one of the backscatter devices 302 may be woken to backscatter. This data is received by the next scheduled general sensor devices 307 (or by a dedicated general sensor device 307). That general sensor device 307, in its own slot, then transmits its own data plus the aggregated data from the backscatter device 302. In this approach, only a data collector device 304 may be required for the BAN 300.

The $n^{th}$ backscatter device 302N may transmit to general sensor device 307 (n-1). Then, in the next cycle, the general sensor device 307 (n-1) may send its own data along with that of the $n^{th}$ backscatter device 302. The wakeup pattern may be generated by general sensor device 307 which is going to listen to the corresponding backscatter device 302, while the signal transmitted in that slot by the general sensor device 307 is used for excitation of the backscatter device 302. The backscatter device 302 then backscatters to send the backscatter signal 208 using codeword translation. Given that the general sensor device 307 has the original sensor data that it transmitted itself, the general sensor devices 307 may decipher the message included in the backscatter signal 208 (e.g., as shown in FIG. 4 with respect to the tag decoder 404).

A separate device may alternatively be used to generate wakeup patterns and continuous excitation signal 206 for the backscatter devices 302. This separate device may be used, for example, only in the first data transmission cycle, because after that the backscatter devices 302 may wake themselves up periodically. Further, the data collector device 304 may also transmit a broadcast wakeup pattern at beginning of every data cycle to synchronize the backscatter devices 302.

FIG. 8A illustrates an example of a configuration Beacon C message for the architecture including data aggregation. As shown, the Beacon C message is similar to the Beacon C message without data aggregation.

FIG. 8B illustrates an example of a CS message for the architecture including data aggregation. As compared to the CS message without aggregation, this CS message includes frequency channel/offsets and time offset for transmission as well as for reception.

FIG. 8C illustrates an example of a CB for backscatter devices 302 for the architecture including data aggregation. As shown, the CB message is similar to the CB message without data aggregation.

FIG. 8D illustrates an example of a Beacon D for the architecture including data aggregation. As shown, the Beacon D is again similar to the Beacon D without data aggregation.

FIG. 8E illustrates an example of a DS for the architecture including data aggregation. As shown, this DS message additionally includes received sensor data from a backscatter device 302, in addition to the sensor data for the general sensor device 307 itself.

FIG. 8F illustrates an example of a backscatter data message (DB) for the architecture including data aggregation. This message is similar to the DS message for the architecture without data aggregation.

FIG. 8G illustrates an example of periodic message scheduling for data transfer in a pipeline enabled, single receiver architecture with data aggregation. As shown for the configuration phase, a first source begins by sending the Beacon C messages (as shown in FIG. 8A) and the CS messages (as shown in FIG. 8B) to configure each sensor when to wakeup. Once the configuration phase is complete, in the data collection phase the first source sends the Beacon D messages (as shown in FIG. 8D) to signal beginning of data collection phase. Each sensor then sends DS messages (as shown in FIG. 8E) including data aggregation (e.g., including data from the previous DB messages of the corresponding backscatter devices 302) during their pre-assigned slot, while the second source sends DB messages (as shown in FIG. 8F) concurrently. The first set of DB messages may also be combined with CB messages (as shown in FIG. 8C) to allow for the setting of the wakeup patterns for the backscatter devices 302.

Figure 9:
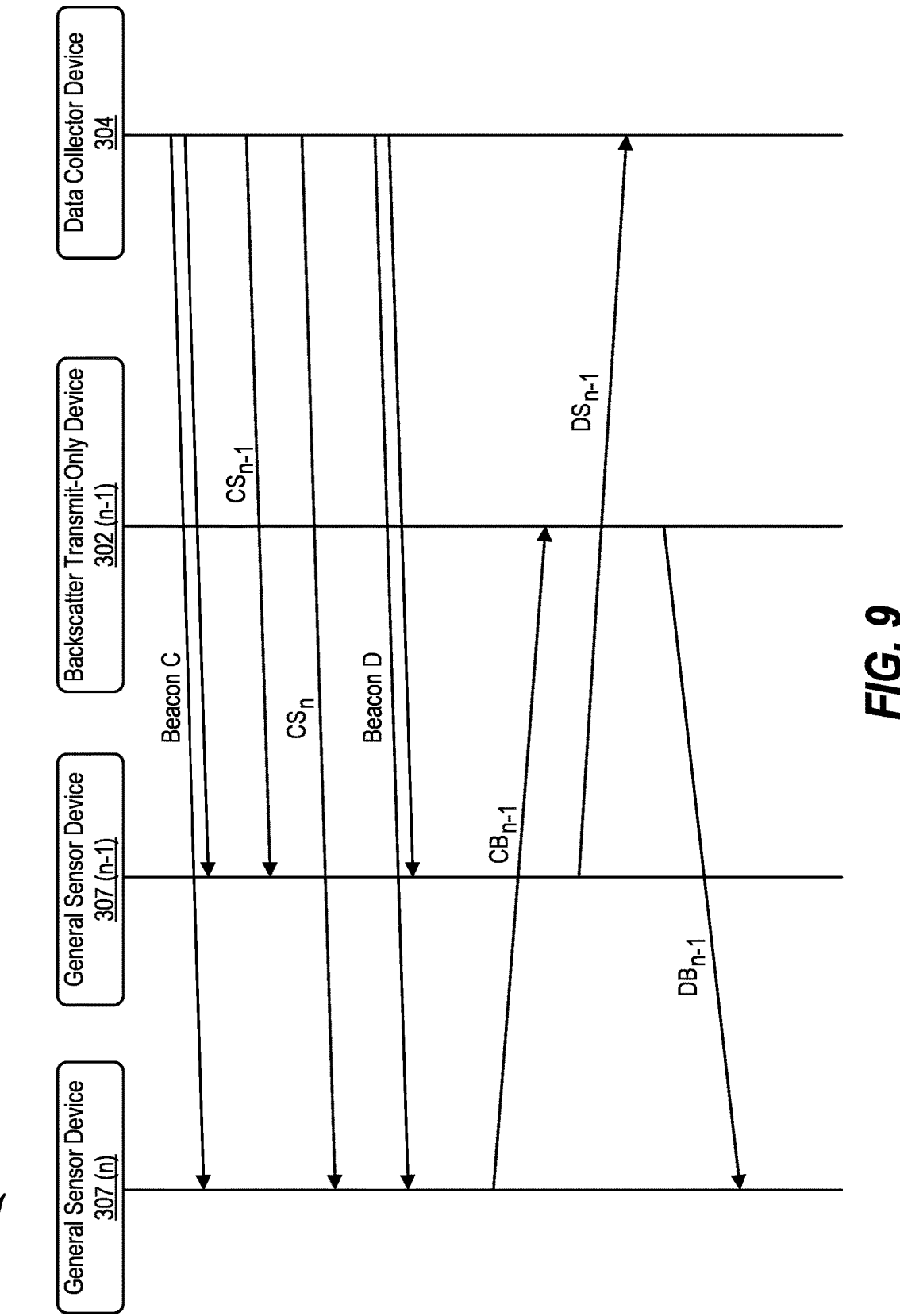
FIG. 9 illustrates an example of periodic message scheduling for data transfer for the architecture including data aggregation.

FIG. 9 illustrates an example data flow diagram 900 of the periodic message scheduling for data transfer in a pipeline enabled, single receiver architecture with data aggregation. First, in the configuration phase, the data collector device 304 sends the Beacon C messages which are received by each of the general sensor devices 307. Next, the data collector device 304 sends the $CS_1$-$CS_n$ messages, which are received by the corresponding general sensor devices 307 (1 through n). Once that phase is complete, in the data collection phase the data collector device 304 sends Beacon D messages to the sensor general sensor devices 307. The general sensor devices 307, in turn, send the CB messages to the backscatter devices 302 to configure the backscatter devices 302. The backscatter devices 302 then send DB messages to the general sensor devices 307 in response, e.g., according to the configured time offsets and excitation signals 206 (e.g., which may be the transmissions from the general sensor devices 307 of the previous set of data). The content of these DB messages may then be compiled into the DS messages sent from the general sensor devices 307 to the data collector device 304.

It should be noted that the pipeline architectures may be especially useful when the number of backscatter devices 302 is equal to or less than the number of general sensor devices 307 in the BAN 300.

It should also be noted that, to achieve power optimization, the sensor devices may be equipped with a backscatter capability. In this case, the devices may take turns toggling between general sensor device 307 mode and backscatter device 302 modes. In an example, a general sensor device 307 which is transmitting more frequently may switch itself to backscatter device 302 mode and may use all backscatter time slots for data communication in the pipelined architecture to achieve power optimization.

It should further be noted that in all the aforementioned architectures, an additional guard band may be used before every backscatter device 302 when they are explicitly woken up to receive wakeup signal pattern. In some examples, the backscatter devices 302, data collector devices 304, excitation devices 306, and general sensor devices 307 may also enable data encoding in which case they send either processed data or only differential data in their time slots to optimize their own respective overall transmissions.

Thus, sensors 102 with backscatter functionality may be utilized in a BAN 300 to provide an order of magnitude of power savings for wireless communication. To support various quality of service requirements, the management of the backscatter devices 302 may be accomplished using various architectures, including: a no pipeline, single radio receiver architecture; a no pipeline, single radio receiver architecture with a dedicated wakeup source; pipeline enabled, a two receiver/receiver with two radios architecture; and a pipeline enabled, single receiver architecture with data aggregation.

Figure 10:
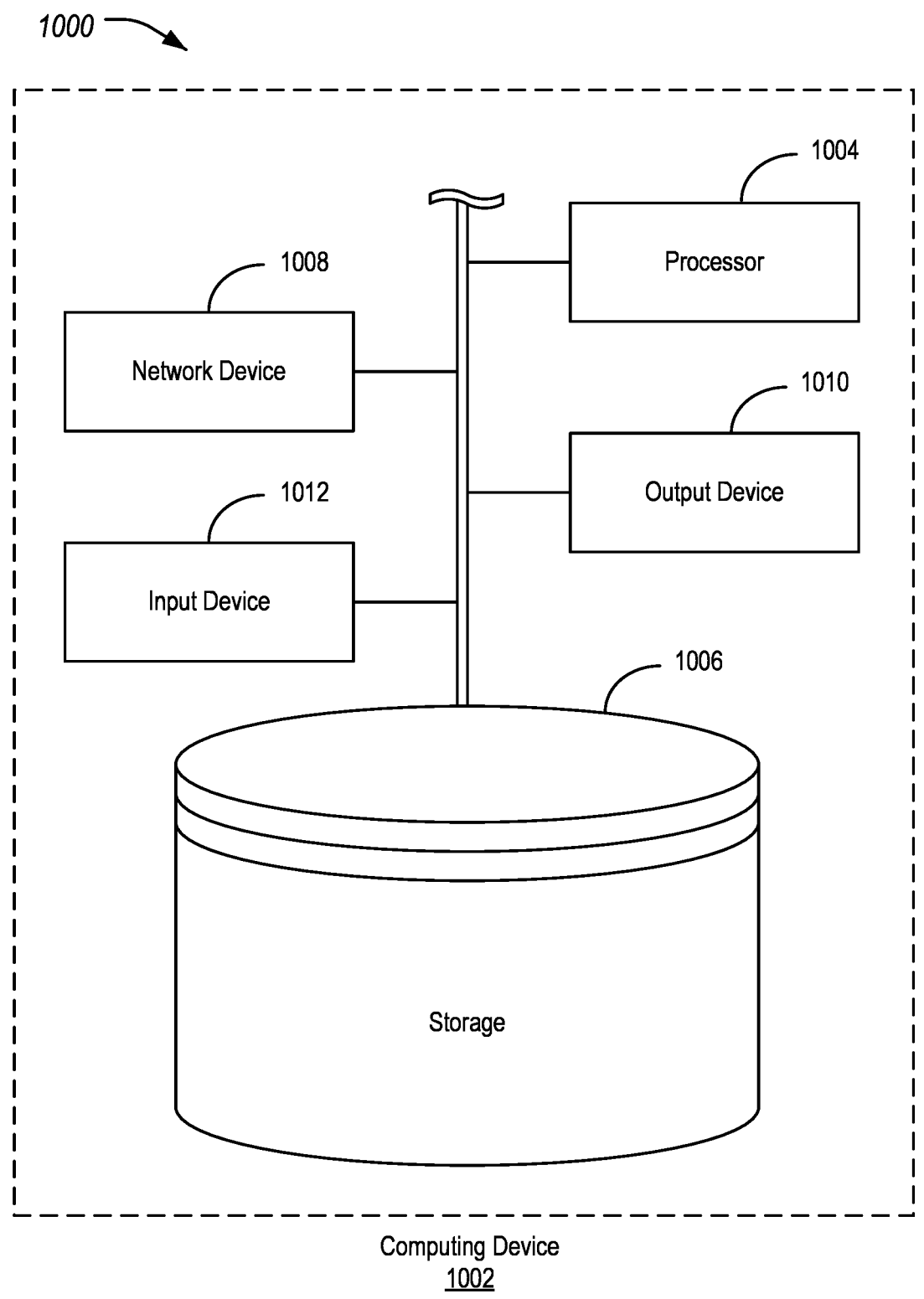
FIG. 10 illustrates an example of a computing device for use in the body area network architectures.

FIG. 10 illustrates an example 1000 of a computing device 1002 for use in the BAN 300 architectures. Referring to FIG. 10, and with reference to FIGS. 1-9, the sensors 102, backscatter devices 302, data collector devices 304, general sensor devices 307, wakeup devices 402, etc., may be examples of such computing devices 1002. As shown, the computing device 1002 includes a processor 1004 that is operatively connected to a storage 1006, a network device 1008, an output device 1010, and an input device 1012. It should be noted that this is merely an example, and computing devices 1002 with more, fewer, or different components may be used.

The processor 1004 may include one or more integrated circuits that implement the functionality of a central processing unit (CPU) and/or graphics processing unit (GPU). In some examples, the processors 1004 are a system on a chip (SoC) that integrates the functionality of the CPU and GPU. The SoC may optionally include other components such as, for example, the storage 1006 and the network device 1008 into a single integrated device. In other examples, the CPU and GPU are connected to each other via a peripheral connection device such as peripheral component interconnect (PCI) express or another suitable peripheral data connection. In one example, the CPU is a commercially available central processing device that implements an instruction set such as one of the x86, ARM, Power, or microprocessor without interlocked pipeline stage (MIPS) instruction set families.

Regardless of the specifics, during operation the processor 1004 executes stored program instructions that are retrieved from the storage 1006. The stored program instructions, accordingly, include software that controls the operation of the processors 1004 to perform the operations described herein. The storage 1006 may include both non-volatile memory and volatile memory devices. The non-volatile memory includes solid-state memories, such as not and (NAND) flash memory, magnetic and optical storage media, or any other suitable data storage device that retains data when the system is deactivated or loses electrical power. The volatile memory includes static and dynamic random-access memory (RAM) that stores program instructions and data during operation of the system 100.

The GPU may include hardware and software for display of at least two-dimensional (2D) and optionally 3D graphics to the output device 1010. The output device 1010 may include a graphical or visual display device, such as an electronic display screen, projector, printer, or any other suitable device that reproduces a graphical display. As another example, the output device 1010 may include an audio device, such as a loudspeaker or headphone. As yet a further example, the output device 1010 may include a tactile device, such as a mechanically raiseable device that may, in an example, be configured to display braille or another physical output that may be touched to provide information to a user.

The input device 1012 may include any of various devices that enable the computing device 1002 to receive control input from users. Examples of suitable input devices that receive human interface inputs may include keyboards, mice, trackballs, touchscreens, voice input devices, graphics tablets, and the like.

The network devices 1008 may each include any of various devices that enable those devices to send and/or receive data from external devices over networks. Examples of suitable network devices 1008 include an Ethernet interface, a Wi-Fi transceiver, a cellular transceiver, or a BLUETOOTH or BLE transceiver, ultra-wideband (UWB) transceiver, or other network adapter or peripheral interconnection device that receives data from another computer or external data storage device, which can be useful for receiving large sets of data in an efficient manner.

The processes, methods, or algorithms disclosed herein can be deliverable to/implemented by a processing device, controller, or computer, which can include any existing programmable electronic control unit or dedicated electronic control unit. Similarly, the processes, methods, or algorithms can be stored as data and instructions executable by a controller or computer in many forms including, but not limited to, information permanently stored on non-writable storage media such as read-only memory (ROM) devices and information alterably stored on writeable storage media such as floppy disks, magnetic tapes, compact discs (CDs), RAM devices, and other magnetic and optical media. The processes, methods, or algorithms can also be implemented in a software executable object. Alternatively, the processes, methods, or algorithms can be embodied in whole or in part using suitable hardware components, such as an ASIC, field-programmable gate array (FPGA), state machines, controllers or other hardware components or devices, or a combination of hardware, software and firmware components.

While exemplary embodiments are described above, it is not intended that these embodiments describe all possible forms encompassed by the claims. The words used in the specification are words of description rather than limitation, and it is understood that various changes can be made without departing from the spirit and scope of the disclosure. As previously described, the features of various embodiments can be combined to form further embodiments of the invention that may not be explicitly described or illustrated. While various embodiments could have been described as providing advantages or being preferred over other embodiments or prior art implementations with respect to one or more desired characteristics, those of ordinary skill in the art recognize that one or more features or characteristics can be compromised to achieve desired overall system attributes, which depend on the specific application and implementation. These attributes can include, but are not limited to strength, durability, life cycle, marketability, appearance, packaging, size, serviceability, weight, manufacturability, ease of assembly, etc. As such, to the extent any embodiments are described as less desirable than other embodiments or prior art implementations with respect to one or more characteristics, these embodiments are not outside the scope of the disclosure and can be desirable for particular applications.

What is claimed is:

1. A method for configuring and utilizing a body area network (BAN), comprising:
in a configuration phase, sending configuration messages for scheduling a plurality of backscatter devices such that during a data collection phase each of the plurality of backscatter devices is configured to backscatter from an excitation signal in an individually-assigned time slot; and in the data collection phase, receiving, to a data collector device from the plurality of backscatter devices, sensor data messages including sensor data from the backscatter devices, the sensor data messages being scheduled according to the configuration phase,
wherein the configuration messages include a timestamp to synchronize system clocks of the plurality of backscatter devices.

2. The method of claim 1, further comprising:
in the data collection phase, sending data period beacon messages for scheduling the plurality of backscatter devices to indicate a beginning of a data transfer cycle.

3. The method of claim 1, further comprising:
in the configuration phase, sending the configuration messages for scheduling a plurality of general sensor devices having transmit and receive functionality, such that during the data collection phase each of the plurality of general sensor devices is also configured to transmit in an individually-assigned time slot.

4. The method of claim 3, further comprising in the data collection phase:
receiving, to each one of the general sensor devices from a respective one of the plurality of backscatter devices, backscatter sensor data messages including received sensor data from the backscatter devices; and
sending, to the data collector device from the general sensor devices, general device sensor data messages including sensor data captured by the general sensor devices and also the received sensor data from the backscatter devices.

5. The method of claim 4, wherein the configuration messages for scheduling the plurality of general sensor devices are sent in a different channel from the configuration messages for scheduling the plurality of backscatter devices.

6. The method of claim 4, wherein the backscatter sensor data messages are modulated on the general device sensor data messages as the excitation signal.

7. The method of claim 1, wherein the configuration messages include a total number of the plurality of backscatter devices and/or an offset value to indicate a beginning of the data collection phase.

8. The method of claim 1, wherein the configuration messages are sent from the data collector device.

9. The method of claim 1, wherein the configuration messages are sent from an excitation device.

10. A system for configuring and utilizing a body area network (BAN), comprising:
a plurality of backscatter devices; and
a data collector device, wherein
in a configuration phase, the plurality of backscatter devices are configured to receive configuration messages for scheduling transmissions of the plurality of backscatter devices, such that during a data collection phase each of the plurality of backscatter devices is configured to transmit in an individually-assigned time slot, and
in the data collection phase, the data collector device is configured to receive, from the plurality of backscatter devices, sensor data messages including sensor data from the backscatter devices, the sensor data messages being scheduled according to the configuration phase,
wherein the configuration messages include a timestamp to synchronize system clocks of the plurality of backscatter devices.

11. The system of claim 10, wherein in the data collection phase, the plurality of backscatter devices are configured to send the sensor data messages responsive to receipt of data period beacon messages, the data period beacon messages indicating a beginning of a data transfer cycle.

12. The system of claim 10, further comprising:
a plurality of general sensor devices having transmit and receive functionality,
wherein in the configuration phase, the plurality of general sensor devices are configured to receive the configuration messages to schedule the plurality of general sensor devices to transmit in individually-assigned time slots of the data collection phase.

13. The system of claim 12, wherein in the data collection phase:
each one of the general sensor devices is configured to:
receive, from a respective one of the plurality of backscatter devices, backscatter sensor data messages including received sensor data from the respective one of the plurality of backscatter devices; and
send, to the data collector device, general device sensor data messages including sensor data captured by the general sensor devices and also the received sensor data from the backscatter devices.

14. The system of claim 13, wherein the configuration messages for scheduling the plurality of general sensor devices are sent in a different channel from the configuration messages for scheduling the plurality of backscatter devices.

15. The system of claim 13, wherein the backscatter sensor data messages are modulated on the general device sensor data messages as an excitation signal.

16. The system of claim 10, wherein the configuration messages include a total number of the plurality of backscatter devices and/or an offset value to indicate a beginning of the data collection phase.

17. The system of claim 10, wherein the configuration messages are sent from the data collector device.

18. The system of claim 10, wherein the configuration messages are sent from an excitation device.

19. A method for configuring and utilizing a body area network (BAN), comprising:
in a configuration phase, sending configuration messages for scheduling a plurality of backscatter devices such that during a data collection phase each of the plurality of backscatter devices is configured to backscatter from an excitation signal in an individually-assigned time slot; and
in the data collection phase, sending data period beacon messages for scheduling the plurality of backscatter devices to indicate a beginning of a data transfer cycle and receiving, to a data collector device from the plurality of backscatter devices, sensor data messages including sensor data from the backscatter devices, the sensor data messages being scheduled according to the configuration phase.

20. The method of claim 19, further comprising:
in the configuration phase, sending the configuration messages for scheduling a plurality of general sensor devices having transmit and receive functionality, such that during the data collection phase each of the plurality of general sensor devices is also configured to transmit in an individually-assigned time slot.

21. The method of claim 20, further comprising in the data collection phase:
receiving, to each one of the general sensor devices from a respective one of the plurality of backscatter devices, backscatter sensor data messages including received sensor data from the backscatter devices; and sending, to the data collector device from the general sensor devices, general device sensor data messages including sensor data captured by the general sensor devices and also the received sensor data from the backscatter devices.

22. The method of claim 21, wherein the configuration messages for scheduling the plurality of general sensor devices are sent in a different channel from the configuration messages for scheduling the plurality of backscatter devices.

23. The method of claim 21, wherein the backscatter sensor data messages are modulated on the general device sensor data messages as the excitation signal.

24. A system for configuring and utilizing a body area network (BAN), comprising:
a plurality of backscatter devices; and
a data collector device, wherein
in a configuration phase, the plurality of backscatter devices are configured to receive configuration messages for scheduling transmissions of the plurality of backscatter devices, such that during a data collection phase each of the plurality of backscatter devices is configured to transmit in an individually-assigned time slot, and
in the data collection phase, the data collector device is configured to
receive, from the plurality of backscatter devices, sensor data messages including sensor data from the backscatter devices, the sensor data messages being scheduled according to the configuration phase, and
send sensor data messages responsive to receipt of data period beacon messages, the data period beacon messages indicating a beginning of a data transfer cycle.

25. The system of claim 24, wherein in the data collection phase, the plurality of backscatter devices are configured to send the sensor data messages responsive to receipt of data period beacon messages, the data period beacon messages indicating a beginning of a data transfer cycle.

26. The system of claim 24, further comprising:
a plurality of general sensor devices having transmit and receive functionality,
wherein in the configuration phase, the plurality of general sensor devices are configured to receive the configuration messages to schedule the plurality of general sensor devices to transmit in individually-assigned time slots of the data collection phase.

27. The system of claim 26, wherein in the data collection phase:
each one of the general sensor devices is configured to:
receive, from a respective one of the plurality of backscatter devices, backscatter sensor data messages including received sensor data from the respective one of the plurality of backscatter devices; and
send, to the data collector device, general device sensor data messages including sensor data captured by the general sensor devices and also the received sensor data from the backscatter devices.

28. The system of claim 24, wherein the configuration messages for scheduling the plurality of general sensor devices are sent in a different channel from the configuration messages for scheduling the plurality of backscatter devices.

29. The system of claim 24, wherein the backscatter sensor data messages are modulated on the general device sensor data messages as an excitation signal.

* * * * *